United States Patent
Dahl et al.

(10) Patent No.: US 6,696,475 B2
(45) Date of Patent: *Feb. 24, 2004

(54) SUBSTITUTED PHENYL DERIVATIVES, THEIR PREPARATION AND USE

(75) Inventors: Bjarne H. Dahl, Allerød (DK); Palle Christophersen, Ballerup (DK)

(73) Assignee: NeuroSearch A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/923,458

(22) Filed: Aug. 8, 2001

(65) Prior Publication Data

US 2002/0037905 A1 Mar. 28, 2002

Related U.S. Application Data

(63) Continuation-in-part of application No. 09/402,165, filed on Sep. 30, 1999, now Pat. No. 6,297,261, and a continuation-in-part of application No. 09/837,166, filed on Apr. 19, 2001, which is a continuation of application No. PCT/DK99/00575, filed on Oct. 19, 1999.

(30) Foreign Application Priority Data

Apr. 22, 1997 (DK) ................................ 0452/97
Apr. 21, 1998 (WO) .............................. PCT/DK98/00162
Oct. 22, 1998 (DK) ........................................ 1998 01362

(51) Int. Cl.$^7$ ......................... A61K 31/44; A61K 31/41; C07D 257/04
(52) U.S. Cl. ..................... 514/381; 514/340; 514/361; 514/362; 514/384; 544/314; 546/268.4; 548/136; 548/144; 548/187; 548/213; 548/243; 548/253; 548/264.2; 548/269.4; 548/319.5; 548/370.1; 549/418
(58) Field of Search ................ 546/268.4; 544/314; 548/144, 136, 187, 253, 264.2, 269.4, 213, 243, 319.5, 370.1; 549/418; 514/340, 381, 384, 361, 362

(56) References Cited

U.S. PATENT DOCUMENTS

| 4,889,612 A | 12/1989 | Geist et al. | 204/466 |
| 4,994,493 A | 2/1991 | Greger et al. | 514/567 |
| 5,273,992 A | 12/1993 | Brugnara et al. | 514/398 |
| 5,362,744 A | 11/1994 | Purchase, Jr. et al. | 514/381 |
| 5,489,612 A | 2/1996 | Atwood et al. | 514/569 |

FOREIGN PATENT DOCUMENTS

| DE | A1-4447096 | 7/1996 |
| EP | A1-0022958 | 1/1981 |
| EP | A1-0028099 | 5/1981 |
| FR | 2 100 943 A | 3/1972 |
| FR | 7126929 | 3/1972 |
| GB | 1055786 | 1/1967 |
| GB | A2290235 | 12/1995 |
| HU | 9202864 | 11/1992 |
| IE | 910745 | 9/1991 |
| WO | WO89/12622 | 12/1989 |
| WO | WO94/22807 | 10/1994 |
| WO | WO96/16647 A2 | 6/1996 |
| WO | WO96/25157 | 8/1996 |
| WO | 9745111 | 12/1997 |
| WO | 9745400 | 12/1997 |
| WO | WO98/47879 | 10/1998 |
| WO | 9932463 | 7/1999 |

OTHER PUBLICATIONS

Chemical Abstracts, vol 113:162396, Jpn. Kokai Tokyo Koho JP 02020856, Jan. 24, 1990.*
Keeling et al., Ann. NY Acad. Sci., vol. 834 (1997) pp. 600–608.
Clohisy et al., J. Orthopaedic Res., vol. 14 (1996) pp. 396–402.
Wangemann et al., Chem. Abstr., vol. 197, No. 107:89293w, p. 21 (1987).
Schlesinger et al., J. Biol. Chem., vol. 272, No. 20, pp. 18636–18643 (1997).
Berkowitz et al., Blood Cells, vol. 8, pp. 283–288 (1982).
Mano et al., Biochem. and Biophys. Res. Comm., vol. 223, pp. 637–642 (1996).
Kameda et al., J. Exp. Med., vol. 186, No. 4, pp. 489–495 (1997).
Ohba et al., FEBS Letters, vol. 387, pp. 175–178 (1996).
Chemical Abstracts, vol. 113:162396; Jpn. Kokai Tokyo Koho JP 02020856 (1990).

* cited by examiner

*Primary Examiner*—Bernard Dentz
(74) *Attorney, Agent, or Firm*—Birch, Stewart, Kolasch & Birch, LLP.

(57) ABSTRACT

The present invention discloses compounds having the formula

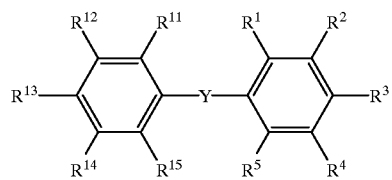

wherein the substituents are defined in the application.

The compounds are useful as chloride channel blockers.

13 Claims, No Drawings

SUBSTITUTED PHENYL DERIVATIVES, THEIR PREPARATION AND USE

This application is a continuation-in-part of application No. 09/402,165, filed on Sep. 30, 1999 now U.S. Pat. No. 6,297,261, No. 09/837,166, filed on Apr. 19, 2001, which is a continuation of PCT/DK99/00575 filed on Oct. 19, 1999, the entire contents of which are hereby incorporated by reference.

The present invention relates to novel substituted phenyl derivatives which are potent chloride channel blockers and as such useful in the treatment of sickle cell anaemia, brain oedema following ischaemia or tumours, diarrhea, hypertension (diuretic), bone metabolic disorders, osteoclast associated disorders and for the reduction of the intraocular pressure for the treatment of disorders such as glaucoma.

BACKGROUND

Chloride channels serve a wide variety of specific cellular functions. Thus, chloride channels contribute to the normal function of skeletal and smooth muscle cells. Blockers of chloride channels are known to be useful in the treatment of brain oedema following ischaemia or tumours, diarrhea, hypertension (diuretic), sickle cell anaemia, bone metabolic disorders, bone metastasizing cancers and in general osteoclast associated disorder as well as for the reduction of the intraocular pressure in disorders such as glaucoma. The compounds of the invention may also be useful in the treatment of allergic and inflammatory conditions and for the promotion of wound healing.

Sickle Cell Anaemia

The use of blockers of chloride channels for the treatment sickle-cell anaemia form a new therapeutic approach.

Sickle cell anaemia and the existence of sickle haemoglobin was the first genetic disease to be understood at the molecular level. The genetic defect underlying sickle cell anaemia causes the substitution of a single amino acid resulting in a mutant haemoglobin, sickle haemoglobin.

The physical manifestations of sickle cell disease is anaemia and painful ischaemic crises due to occlusion of the microcirculation by deformed erythrocytes (sickle cells). The primary cause of sickle erythrocyte deformation and distortion (or sickling) is a reversible polymerisation and gelation of sickle haemoglobin induced at the low oxygen tensions prevalent in metabolically active tissues. Sickle cells are also characterised by an enhanced cation permeability, resulting in cation depletion and cellular dehydration. Since the delay time for the polymerisation has been described as an extremely steep function of the sickle haemoglobin concentration itself, any decrease in cell volume will greatly increase the probability of sickling and thereby of vessel occlusion. Compounds which blocks the deoxygenation induced salt and volume (water) loss may delay the sickling process enough to avoid occlusion upon the passage of the sickle erythrocyte through metabolically active tissue. It has been estimated that a delay time of only 10 sec may suffice.

Several membrane ion channels and transporters present in normal erythrocytes have been suggested to participate in the altered membrane permeabilities of sickle cells. The favoured hypothesis has been stimulation of the $Ca^{2+}$-activated $K^+$-channel and several blockers of this channel has been suggested as therapeutic agents for the treatment of sickle-cell anaemia (Effects of Cetiedil on Monovalent Cation Permeability in the Erythrocyte: An explanation for the Efficacy of Cetiedil in the treatment of Sickle Cell Anaemia, Berkowitz, L. R., Orringer, E. P., Blood cells, (283–288 (1982) and U.S. Pat. No. 5.273.992).

Since, $K^+$ efflux through a K-channel must be followed by an equal efflux of $Cl^-$ to maintain electroneutrality, blockade of erythrocyte chloride channels should be as effective as blocking the K-channels itself. An advantage to the use of chloride channel blockers is that salt loss which may occur due to activation of unknown K-channel types will indirectly be blocked too.

The compounds of the present invention are potent blockers of chloride channels as measured by concomitant measurements of conductive neffluxes of chloride and membrane potentials in suspensions of erythrocytes, and the compounds are therefore predicted to be useful in the treatment of sickle-cell disease.

Osteoporosis and Other Osteoclast Associated Disorders.

The bone tissue is constantly renewed by the controlled activity of two cell types, osteoblasts, which lay down the new bone mass, and osteoclasts, which degrade and reabsorb the bone tissue by secretion of proteolytic enzymes such as cathepsin as well as acid, in particular HCl onto the bone surface. In osteoporosis the balance between the degradation and the synthesis is severely disturbed, which results in a progressive loss of bone material and gradual weakening of the skeleton. Clinically, hormone replacement studies has shown that the decline in estrogen levels at the onset of menopause is an important hormonal factor for the triggering of the disease. In vitro studies has shown that the osteoclasts are important targets cells for estrogen (i.e. Mano et al., Biochem. Biophys. Res. Commun. 223(3), 637–642, 1996) and that the hormone inhibits the bone reabsorbing activity of osteoclasts via induction of osteoclast apoptosis (Kameda et al., J. Exp. Med., 186(4), 489–495, 1997) and/or via altered resorbtion capacity of the individual cells. Thus, the major estrogens effect on bone metabolism seems to be an inhibition of bone degradation by a direct effect on the osteoclasts.

Osteoclast Physiology

As an alternative to hormone replacement down regulation of osteoclast acid producing activity by modulators of membrane transporters is an attractive, but hitherto clinical untested possibility. The physiological process whereby the osteoclast secrete HCl—a key event in bone reasorbtion—is relatively well understood and is conceptually similar to epithelial transport. Like epithelia cells osteociasts are morphologically highly polarised cells with membrane transporters asymmetrically distributed between the bone-facing ruffled membrane and the smooth outer membrane. At the border between the ruffled and smooth membrane segments the osteoclast is tightly attached to the bone surface, thus creating a sealed cavity between the cell and the bone surface. Pits are formed beneath the cavity as a result of HCl-induced demineralisation and enzymatic break-down of the bone matrix.

The ultimate event in the osteociast HCl secretion across the ruffled membrane is an active transport of $H^+$ by a vacuolar-type proton pump and a passive transport of $Cl^-$ mediated via an outwardly rectifying Cl-channel. Due to HCl secretion the intracellular pH tend to increase and $Cl^-_i$ tend to decrease, which—if allowed to occur—would quickly lead to cessation of acid secretion. Osteoclasts posses two important back-up systems aimed at maintaining a constant supply of intracellular $H^+$ and $Cl^-$ for the ruffled membrane transporters. First, the cell contains very high concentrations of the cytosolic enzyme carbonic anhydrase II, which catalyses the slow normally quite slow hydration of $CO_2$ to $H_2CO_3$, a molecule which spontaneously dissociate to form $H^+$ and $HCO^-_3$. Second, the osteoclast outer membrane is packed with transporters (AE2), which mediate obligatory $Cl^-/HCO^-_3$ exchange. Hence, $HCO^-_3$ produced by the carbonic anhydrase exzyme is exchanged with extracellular $Cl^-$. Apart from erythrocytes, osteoclasts are the mammalian cell type with the highest expression level of this protein.

In conclusion, the proton pump and the Cl-channel are fed by $H^+$ and $Cl^-$, respectively, via the concerted activity of the carbonic anhydrase and the anion exchanger.

Possible Pharmacological Intervention

In principle, any of the four proteins described above which are directly involved in the transcellular secretion of HCl are valid targets for interference with the resorptive properties of osteoclasts.

Direct block of the proton pump is achievable with the antibiotic bafilomycin A1, which is an extremely potent, reversible inhibitor, whereas omeprazol—an irreversible inhibitor of the proton pump responsible for acid production in the stomach—is ineffective. In vitro bafilomycin A1 completely eliminates bone resorbtion in the bone slice assay pit formation test (Ohba et al, FEBS left. 387(2–3), 175–178, 1996). In vivo the compound depresses bone degration in growing yound rats (Keeling et al, Ann. N. Y. Acad. Sci., 834, 600–608 1997). The general applicability of the compound is limited due to its toxicity, which may be due to undesired inhibition of proton pumps in other areas of the body. Subtypes of the vacuolar proton pump exists, however it is not known if it will be possible to obtain pharmacological selectivity between these isoforms.

Inhibition of the carbonic anhydrase enzyme with acetacolamide is effective in vitro in the pit formation assay (Ohba et al, FEBS left. 387(2–3), 175–178, 1996). Various inhibitors of the kidney carbonic anhydrase enzymes has previously been used as diuretic agents.

It is well established that osteoclast ability for bone resorbtion is highly correleated with the expression of the ruffled membrane Cl-channel (Schlesinger et. al. Jour. Biol. Chem., 272(30), 18636–18643,1997). Block of the ruffled border Cl-channel is only achievable with very high concentratios of stilbene-sulfonates like DIDS, which makes firm conclusions about the efficacy of a selective block questionable, especially since the stilbenes most likely will block the anion exchanger even better than the Cl-channel.

A blockade of the anion exchanger in osteoclasts will also be a regulatory site for osteociast activity optionally in combination with blockade of the chloride channel as a concomitant blockade of both channels or a blockade of either channel alone.

It is also well established that osteoclasts are involved in other bone-tissue related disorders (i.e. Clohisy et. al., J. Orthop. Res., 14(3), 396–702, 1996) and intervention with the osteoclast activity is very likely to prevent these types of disorders. The compounds of the present invention administered alone as well as in combination with other well known treatments of bone metabolism related diseases will have an effect on these diseases.

The compounds of the present invention are potent blockers of chloride channels and also the anion exchanger, as measured by concomitant measurements of conductive netfluxes of chloride and membrane potentials in suspensions of erythrocytes, and the compounds are therefore predicted to be useful in the treatment of sickle-cell disease, osteoporosis as well as other osteoclast associated disorders.

PRIOR ART

Several chloride channel blockers and the use thereof have already been described:

Pflügers Arch (1986), 407 (suppl. 2), pages 128–141 describes several compounds with chloride channel blocking activity. A very potent compound described herein is 5-nitro-2-(3-phenylpropylamino)benzoic acid. The use of chloride channel blockers for the treatment of sickle cell anaemia is not disclosed herein.

U.S. Pat. No. 4,889,612 describes Calixarene derivatives and their use as chloride channel blockers.

U.S. Pat. No. 4,994,493 describes certain 5-nitrobenzoic acid derivatives and their use in the treatment of cerebral oedema.

WO 96/16647 describes the use of chloride channel blockers for reduction of the intraocular pressure and specifically the use of chloride channel blockers for the treatment of glaucoma.

WO 97/45400 describes other phenyl derivatives as chloride channels blockers;

The present invention relates to a series of substituted phenyl derivatives which are potent chloride channel blockers, and their use in the treatment of sickle-cell anaemia and osteoporosis as well as other bone metabolic disorders. The compounds of the present invention are novel and differs as well in the substitution patterns as in pharmacodynamic properties such as kinetic behaviour, bioavailability, solubility and efficacy.

OBJECTS OF THE INVENTION

It is an object of the present invention to provide novel substituted phenyl derivatives and pharmaceutically acceptable salts thereof which are useful in the treatment of disorders or diseases responsive to the blockade of chloride channels.

Still another object of the present invention is to provide a method of treating disorders or diseases responsive to the blockade of chloride channels, such as for example brain oedema following ischaemia or tumours, diarrhea, hypertension (diuretic), glaucoma and in particular sickle cell anaemia and osteoporosis.

SUMMARY OF THE INVENTION

The invention then comprises, inter alia, alone or in combination:

A compound having the following formula (I)

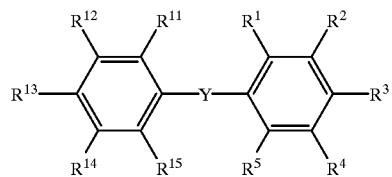

or a pharmaceutically acceptable salt thereof
wherein one of $R^1$, $R^2$ and $R^3$ is a acidic functional group having a pKa value below 8 or a group which is convertible in vivo to such a group;

$R^4$, $R^5$ and the other two substituents $R^1$, $R^2$ and $R^3$ are each independently selected from hydrogen; alkyl; alkoxy; hydroxy; halogen; trifluoromethyl; cyano; nitro; amino; alkylamino, $NHCOR^9$, $CO_2R^9$, $—CON(R^9)_2$, $—NHSO_2—R^9$, $—SO_2N(R^9)_2$ wherein $R^9$ represents hydrogen, alkyl, cycloalkyl, cycloalkylalkyl, alkenyl, alkynyl, aryl, aralkyl, heteroaryl or $R^9$ comprises a 5-8 membered ring optionally containing double bonds and optionally containing one or two heteroatoms, which can be substituted by alkyl or acyl; or $(R^9)_2$ together with the heteroatom to which it is connected represents a 5-8 membered ring optionally containing double bonds and optionally containing another heteroatom which can be substituted by alkyl or acyl; aryl, phenylamino, phenoxy or heteroaryl wherein the phenyl, aryl or heteroaryl group may be substituted one or more times with substituents selected from alkyl, hydroxy, alkoxy, halogen, trifluoromethyl, cyano, nitro, amino, $NHCOR^9$, $CO_2R^9$, $—CON(R^9)_2$, $—NHSO_2—R^9$, $—SO_2N(R^9)_2$ wherein $R^9$ is as defined above; or $R^3$ and $R^4$ or $R^4$ and $R^5$ together form a 4-8 membered saturated or unsaturated ring and the other substituents $R^1$, $R^2$, $R^3$, $R^4$ and $R^5$ is as defined above;

Y represents

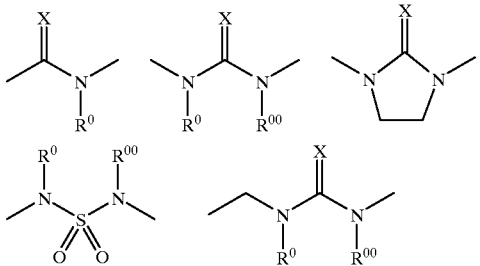

wherein $R^0$ and $R^{00}$ independently represents hydrogen or lower alkyl;

X represents O or S;

$R^6$ is hydrogen, or alkyl;

$R^{11}$, $R^{12}$, $R^{13}$, $R^{14}$ and $R^{15}$ are each independently selected from hydrogen; alkyl; alkoxy; hydroxy; halogen; trifluoromethyl; cyano; nitro; amino; alkylamino; $—COOR^7$; $—NHSO_2$-alkyl; $—SO_2N(R^7)_2$; $—SO_2OR^7$; $—CO—R^7$; aryl, phenylamino, phenoxy or heteroaryl wherein the phenyl, aryl or heteroaryl group may be substituted one or more times with substituents selected from alkyl, hydroxy, alkoxy, halogen, trifluoromethyl, cyano, nitro, amino and alkylamino, $—COOR^7$; $CON(R^7)_2$. $—NHSO_2—R^7$; $—SO_2N(R^7)_2$; $—SO_2OR^7$; $—CO—R^7$, or one of $R^{11}$ and $R^{12}$, $R^{12}$ and $R^{13}$, $R^{13}$ and $R^{14}$ and $R^{14}$ and $R^{15}$ together form a 4-8 membered saturated or unsaturated ring and the other substituents $R^{11}$, $R^{12}$, $R^{13}$, $R^{14}$ and $R^{15}$ is as defined above and wherein $R^7$ represents hydrogen, alkyl, cycloalkyl, cycloalkylalkyl, alkenyl, alkynyl, aryl, aralkyl, heteroaryl or $R^7$ comprises a 5-8 membered ring optionally containing double bonds and optionally containing one or two heteroatoms which can be substituted by alkyl or acyl; or $(R^7)_2$ together with the heteroatom to which it is connected represents a 5-8 membered ring optionally containing double bonds and optionally containing another heteroatom which can be substituted by alkyl or acyl;

a method for the preparation of a compound of formula (I) as above, comprising:

a) reacting a compound having the formula

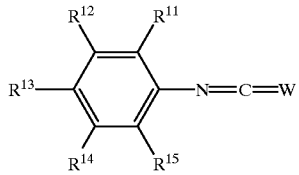

wherein W is O, or S and $R^{11}$, $R^{12}$, $R^{13}$, $R^{14}$ and $R^{15}$ is as defined above, with a compound having the formula

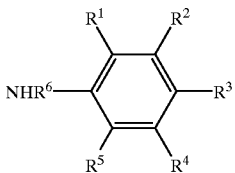

wherein $R^1$, $R^2$ $R^3$, $R^4$, $R^5$ and $R^6$ is as defined above, or b) reacting a compound having the formula

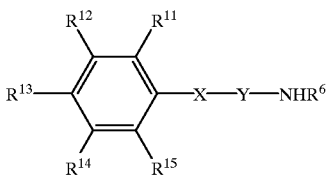

wherein X, Y, $R^6$, $R^{11}$, $R^{12}$, $R^{13}$, $R^{14}$ and $R^{15}$ is as defined above, with a compound having the formula

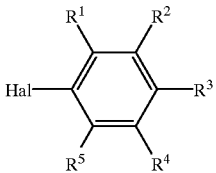

wherein Hal is halogen and $R^1$, $R^2$, $R^3$, $R^4$ and $R^5$ is as defined above, whereafter optionally the compound obtained is converted to another compound of the invention and/or a pharmaceutically acceptable salt thereof is formed using conventional methods;

a compound of the following formula (II):

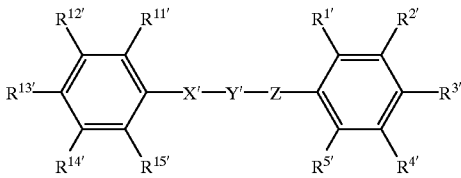

or a pharmaceutically acceptable salt thereof wherein one of $R^1$, $R^2$ and $R^3$ is a cyclic or heterocyclic acidic functional group having a pKa value below 8 or a group which is convertible in vivo to such a group;

$R^{4'}$, $R^{5'}$ and the two other substituents $R^{1'}$, $R^{2'}$ and $R^{3'}$ are each independently selected from hydrogen; alkyl; alkoxy; hydroxy; halogen; trifluoromethyl; cyano; nitro; amino; alkylamino; $—COOR^{7'}$; $—NHSO_2$-alkyl; $—SO_2N(R^{7'})_2$; $—SO_2OR^{7'}$; $—CO—R^{7'}$; aryl, biphenyl, phenylamino, phenoxy or heteroaryl, wherein the aryl, biphenyl, phenylamino, phenoxy or heteroaryl group may be substituted one or more times with substituents selected from alkyl, hydroxy, alkoxy, halogen, trifluoromethyl, cyano, nitro, amino and alkylamino; aryl and heteroaryl, or $R^{3'}$ and $R^{4'}$ or $R^{4'}$ and $R^{5'}$ together form a cyclic structure and the other substituents $R^{1'}$, $R^{2'}$, $R^{3'}$, $R^{4'}$ and $R^{5'}$ is as defined above;

and $R^{7'}$ is hydrogen, alkyl, amino or phenyl;

Y' is $—CO—$, $—CS—$, $—SO_2—$, or $—C(=N—R^{8'})—$, wherein $R^{8'}$ is hydrogen, alkyl, or cyano;

X' is —NH—, —CH₂—NH—, or —SO₂—NH—;
Z is NR⁶', O, —CH═CH—, —N═CH—, or —CH═N—
R⁶' is hydrogen, or alkyl;
R¹¹', R¹²', R¹³', R¹⁴' and R¹⁵' are each independently selected from hydrogen; alkyl; alkoxy; hydroxy; halogen; trifluoromethyl; cyano; nitro; amino; alkylamino; —COOR⁷'; —NHSO₂-alkyl; —SO₂N(R⁷')₂; —SO₂OR⁷'; —CO—R⁷'; aryl, biphenyl, phenylamino, phenoxy or heteroaryl, wherein the aryl, biphenyl, phenylamino, phenoxy or heteroaryl group may be substituted one or more times with substituents selected from alkyl, hydroxy, alkoxy, halogen, trifluoromethyl, cyano, nitro, amino and alkylamino; aryl and heteroaryl, or one of R¹¹' and R¹²', R¹²' and R¹³', R¹³' and R¹⁴' and R¹⁴' and R¹⁵' together form a cyclic structure and the other substituents R¹¹', R¹²', R¹³', R¹⁴' and R¹⁵' is as defined above and R⁷' is as defined above;
a compound as above wherein one of R¹', R²' and R³' is 3-hydroxy-4-oxo-pyranyl, 2-hydroxy-4-oxo-pyrimidyl, 4-hydroxy-1,2,4-triazolyl, 3,5-dioxo-1,2,4-oxadiazolidinyl, 2,4-dioxo-imidazolidinyl, 2,5-dioxo-3-hydroxy-pyrrolyl, 2,5-dioxo-pyrrolidinyl, 2,4-dioxo-1,3-thiazolidinyl, 3-hydroxy-isoxazolyl, 5-hydroxy-isoxazolyl, 3-hydroxy-isothiazolyl, 3-hydroxy-1,2,5-thiadiazolyl, tetrazolyl, 3-hydroxy-triazolyl, 3-hydroxy-pyrazolyl, 2-hydroxy-1,3,4-oxadiazolyl or 2-hydroxy-3,4-dioxo-cyclobutenyl, 3-oxo-1,2-dihydro-1,2,4-trizaolyl, 2-oxo-3H-1,3,4-oxadizolyl, 3-oxo-1,2-dihydro-1,2,4-triazolyl; Z is NR⁶' and Y' is CO;
a method for the preparation of a compound of formula (II) as above, comprising:
a) reacting a compound having the formula

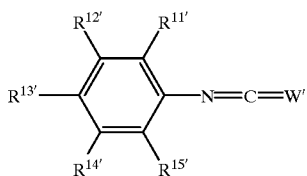

wherein W' is O, or S and R¹¹', R¹²', R¹³', R¹⁴' and R¹⁵' is as defined above, with a compound having the formula

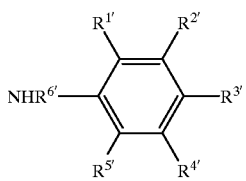

wherein R¹', R²', R³', R⁴', R⁵' and R⁶' is as defined above, or
b) reacting a compound having the formula

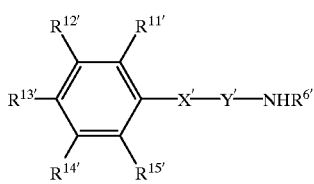

wherein X', Y', R⁶', R¹¹', R¹²', R¹³', R¹⁴' and R¹⁵' is as defined above, with a compound having the formula

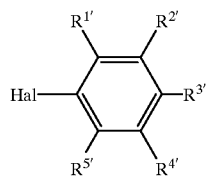

wherein Hal is halogen and R¹', R²', R³', R⁴' and R⁵' is as defined above,
whereafter optionally the compound obtained is converted to another compound of the invention and/or a pharmaceutically acceptable salt thereof is formed using conventional methods;
a chloride channel blocker as above optionally combined with known therapeutic treatment of bone metabolic disorders;
a pharmaceutical composition comprising a therapeutically effective amount of a compound as any above or a pharmaceutically acceptable salt thereof together with at least one pharmaceutically acceptable carrier or diluent;
the use of a compound as above for the preparation of a medicament for the treatment of a disorder or disease of a living animal body, including a human, which disorder or disease is responsive to the blockade of chloride channels;
a method for the treatment of a disorder or disease of a living animal body, including a human, which disorder or disease is responsive to the blockade of chloride channels, comprising administering to such a living animal body in need thereof a therapeutically effective amount of a compound as above;

DETAILED DISCLOSURE OF THE INVENTION

The invention comprises in a preferred aspect a compound of the following formula (I)

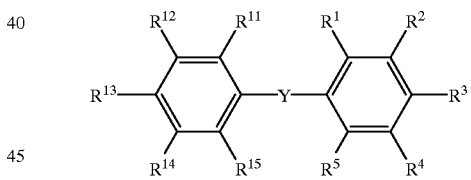

wherein one of R¹, R² and R³ is 3-hydroxy-4-oxo-pyranyl, 2-hydroxy-4-oxo-pyrimidyl, 3,5-dioxo-1,2,4-oxadiazolidinyl, 2,4-dioxo-imidazolidinyl, 2,5-dioxo-3-hydroxy-pyrrolyl, 2,5-dioxo-pyrrolidinyl, 2,4-dioxo-1,3-thiazolidinyl, 3-hydroxy-isoxazolyl, 5-hydroxy-isoxazolyl, 3-hydroxy-isothiazolyl, 3-hydroxy-1,2,5-thiadiazolyl, tetrazolyl, 3-hydroxy-triazolyl, 3-hydroxy-pyrazolyl, 2-hydroxy-1,3,4-oxadiazolyl or 2-hydroxy-3,4-dioxo-cyclobutenyl, NH₂, —COOR¹⁶, —CH₂COOR¹⁶, —CON(R¹⁶)₂, —NHSO₂—R¹⁶, —SO₂N(R¹⁶)₂, —SO₂OR¹⁶, —P₃H₂, —PO₃RH, —PO₂NH₂, —CONHOH, —CONHCN, —CONHSO₂R¹⁶ and —CONHNH₂, wherein R¹⁶ is hydrogen, alkyl, cycloalkyl, cycloalkylalkyl, alkenyl, alkynyl, aryl, aralkyl, heteroaryl or R¹⁶ comprises a 5-8 membered ring optionally containing double bonds and optionally containing one or two heteroatoms, or (R¹⁶)₂ together with the heteroatom to which it is connected represents a 5-8 membered ring optionally containing double bonds and optionally containing another heteroatom; and the other of R¹, R² and R³ is as defined above;

A preferred aspect of the invention comprises compound as above, wherein one of $R^1$, $R^2$ and $R^3$ represents COOH, $CH_2COOR^{16}$, $CON(R^{16})_2$, tetrazolyl, methyltetrazolyl, $-NHSO_2R^{16}$, $CO_2R^{16}$, $CO_2N(R^{16})_2$, $SO_2N(R^{16})_2$, $CONHSO_2R^{16}$; $SO_2OR^{16}$, wherein $R_{16}$ is as defined above;

Another preferred aspect of the invention comprises a compound as above wherein $R^4$, $R^5$ and the remaining of $R^1$, $R^2$ or $R^3$ independently represents hydrogen, alkyl, nitro, amino, alkylamino, $CO_2R^9$, $CF_3$, alkyl, halogen, hydroxy, alkoxy, $NHCOR^9$, $CON(R^9)_2$ aryl optionally substituted with $CON(R^9)_2$, $NHCOR^9$, $SO_2N(R^9)_2$, $CO_2R^9$, wherein $R^9$ is as defined above;

Yet another preferred aspect of the invention comprises a compound as above wherein one or more of $R^{11}$, $R^{12}$, $R^{13}$, $R^{14}$ and $R^{15}$ independently represents $CF_3$, halogen, COOH, $CH_2COOR^{16}$, $CON(R^{16})_2$, $NHSO_2R^{16}$, $CO_2R^{16}$, $CO_2N(R^{16})_2$, $SO_2N(R^{16})_2$, $CONHSO_2R^{16}$; $SO_2OR^{16}$ or aryl optionally substituted with $NHCOR^7$, $CO_2R^7$, $-CON(R^7)_2$, $-NHSO_2-R^7$, $-SO_2N(R^7)_2$ wherein $R^7$ is as defined above; or $R^{11}$ and $R^{12}$ together with the phenyl group to which they are attached forms a 6-membered unsaturated ring; $R^{16}$ and $R^7$ is as defined above;

Y preferentially represents —NHCONH—;

In a preferred aspect of the invention

Y represents —NHCONH—; $R^1$ represents tetrazolyl, and $R^3$ represents halogen, in particular Bromo; or $R^3$ represents phenyl which is substituted by $SO_2N(R^{16})_2$ wherein $R^{16}$ is hydrogen, alkyl, cycloalkyl, cycloalkylalkyl or $R^{16}$ comprises a 5-8 membered ring optionally containing double bonds and optionally containing one heteroatom, or $(R^{16})_2$ together with the heteroatom to which it is connected represents a 5-8 membered ring optionally containing double bonds and optionally containing another heteroatom which can be substituted by alkyl or acyl;

In yet another preferred aspect of the invention Y represents —NHCONH—; $R^{12}$ represents $CF_3$, or halogen, in particular bromo or chloro; $R^{13}$ represents hydrogen or halogen in particular chloro; and $R^{14}$ represents hydrogen or $CF_3$;

The most preferred aspect of the invention comprises the following compounds:

N-phenyl-N'-(2-carboxyphenyl) urea;
N-(3-trifluoromethylphenyl)-N'-(2-carboxyphenyl)-N-methyl urea;
N-(3-trifluoromethylphenyl)-N'-(4-bromo-2-carboxyphenyl) urea;
N-(3-trifluoromethylphenyl)-N'-(2-carboxy-4-chlorophenyl) urea;
N-(3-rifluoromethylphenyl)-N'-(2-carboxy-4-fluorophenyl) urea;
N-(3-bromophenyl)-N'-(2-(1-H-tetrazol-5-yl)-4-biphenyl) urea;
N-(3-trifluoromethylphenyl)-N'-(4'-(N,N-dimethylsulfamoyl)-2-(1-H-tetrazol-5-yl)-4-biphenyl) urea;
N-(3-bromophenyl)-N'-(4'-(N,N-dimethylsulfamoyl)-2-(1-H-tetrazol-5-yl)-4-biphenyl) urea;
N-(3-bromophenyl)-N'-(4'-(N,N-dimethylcarbamoyl)-2-(1-H-tetrazol-5-yl)-4-biphenyl) urea;
N-(3-trifluromethylphenyl)-N'-(4-amino-2-(1-H-tetrazol-5-yl)phenyl) urea;
N-(3-trifluoromethylphenyl)-N'-(4-acetylamino-2-(1-H-tetrazol-5-yl)phenyl) urea;
N-(3-trifluoromethylphenyl)-N'-(4'-carbamoyl-2-(1-H-tetrazol-5-yl)-4-biphenyl) urea;
N-(3-trifluoromethylphenyl)-N'-(4'-(N,N-dimethylcarbamoyl)-2-(1-H-tetrazol-5-yl)-4-biphenyl) urea;
N-(3-trifluoromethylphenyl)-N'-(4'-carboxy-2-(1-H-tetrazol-5-yl)-4-biphenyl) urea;
N-(3-trifluoromethylphenyl)-N'-(4 '-(N-phenylcarbamoyl)-2-(5-tetrazoyl)-4-biphenyl) urea;
N-(2-indan)-N'-(2-(1-H-tetrazol-5-yl)phenyl) urea;
N-(4-biphenyl)-N'-(2-(1-H-tetrazol-5-yl)phenyl) urea;
N-(3-biphenyl)-N'-(2-(1-H-tetrazol-5-yl)phenyl) urea;
N-(3-acetylphenyl)-N'-(2-(1-H-tetrazol-5-yl)phenyl) urea;
N-(3-trifluoromethylphenyl)-N'-(2-(1-methyltetrazol-5-yl)-4-biphenyl) urea;
N-(3-biphenyl)-N'-(4-bromo-2-(1-H-tetrazol-5-yl)phenyl) urea;
N-(3-(3-pyridyl)phenyl)-N'-(4-bromo-2-(1-H-tetrazol-5-yl)phenyl) urea hydrochloride;
N-(3-bromophenyl)-N'-(4-bromo-2-(1-H-tetrazol-5-yl)phenyl) urea;
N-(3-bromophenyl)-N'-[3'-nitro-2-(1-H-tetrazol-5-yl)-biphenyl] urea;
N-(3-bromophenyl)-N'-[4'-(sulfoamido-N-methylpiperazinium chloride)-2-(1-H-tetrazol-5-yl)-4-biphenyl] urea;
N-(3-bromophenyl)-N'-[4'-carbamoyl-N-methylpiperazine)-2-(1-H-tetrazol-5-yl)-4'-biphenyl] urea;
N-(3,5-dichlorophenyl)-N'-[4-bromo-2-(1H-tetrazol-5-yl)phenyl] urea;
N-(4-trifluoromethylphenyl-N'-[4-bromo-2-(1-H-tetrazol-5-yl)phenyl] urea;
N-(4-bromophenyl)-N'-[4-bromo-2-(1-H-tetrazol-5-yl)phenyl] urea;
N-(3-methoxyphenyl)-N'-[4-bromo-2-(1-H-tetrazol-5-yl)phenyl] urea;
N-(3-chlorophenyl)-N'-[4-bromo-2-(1-H-tetrazol-5-yl)phenyl] urea;
N-(3-methylphenyl)-N'-[4-bromo-2-(1-H-tetrazol-5-yl)phenyl] urea;
N-(3,4-dichlorophenyl)-N'-[4-bromo-2-(1-H-tetrazol-5-yl)phenyl] urea;
N-(2-naphthyl)-N'-[4-bromo-2-(1-H-tetrazol-5-yl)phenyl] urea;
N-(4-methyl-3-nitrophenyl)-N'-[4-bromo-2-(1-H-tetrazol-5-yl)phenyl] urea;
N-(2-chloro-4-trifluoromethylphenyl)-N'-[4-bromo-2-(1-H-tetrazol-5-yl)phenyl] urea;
N-(3,5-di(trifluoromethyl)phenyl)-N'-[4-bromo-2-(1-H-tetrazol-5-yl)phenyl] urea;
N-(3,5-di methylphenyl)-N'-[4-bromo-2-(1-H-tetrazol-5-yl) phenyl] urea;
N-(4-ethoxyphenyl)-N'-[4-bromo-2-(1-H-tetrazol-5-yl) phenyl] urea;
N-(4-methoxyphenyl)-N'-[4-bromo-2-(1H-tetrazol-5-yl) phenyl] urea;
N-(2-trifluoromethylphenyl)-N'-[4-bromo-2-(1-H-tetrazol-5-yl)phenyl] urea;
N-(2-bromophenyl)-N'-[4-bromo-2-(1-H-tetrazol-5-yl) phenyl] urea;
N-(2-chlorophenyl)-N'-[4-bromo-2-(1-H-tetrazol-5-yl) phenyl] urea;
N-(2-fluorophenyl)-N'-[4-bromo-2-(1-H-tetrazol-5-yl) phenyl] urea;
N-(4-chloro-3-trifluoromethylphenyl)-N'-[4-bromo-2-(1H-tetrazol-5-yl)phenyl] urea;
N-(3-bromophenyl)-N'-(2,3-difluorophenyl) urea;
N-(2-methylphenyl)-N'-[4-bromo-2-(1-H-tetrazol-5-yl) phenyl] urea;

N-(2-ethylphenyl)-N'-[4-bromo-2-(1-H-tetrazol-5-yl) phenyl] urea;
N-(4-methylphenyl)-N'-[4-bromo-2-(1-H-tetrazol-5-yl) phenyl] urea;
N-(2-nitrophenyl)-N'-[4-bromo-2-(1-H-tetrazol-5-yl) phenyl] urea;
N-(3-fluorophenyl)-N'-[4-bromo-2-(1-H-tetrazol-yl)phenyl] urea;
N-(4-[2-propyl]phenyl)-N'-[4-bromo-2-(1-H-tetrazol-5-yl) phenyl] urea;
N-(3-nitrophenyl)-N'-[4-bromo-2-(5-tetrazol-5-yl)phenyl] urea;
N-(3-acetylphenyl)-N'-[4-bromo-2-(1-H-tetrazol-5-yl) phenyl] urea;
N-(4-nitrophenyl)-N'-[4-bromo-2-(1-H-tetrazol-5-yl) phenyl] urea;
and pharmaceutically acceptable addition salts of any of the compounds above;

The invention comprises in another preferred aspect a compound of the following formula (II)

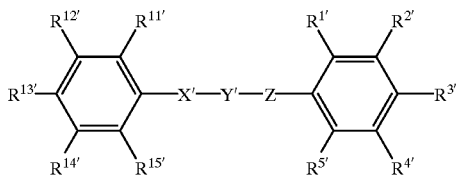

or a pharmaceutically acceptable salt thereof
wherein one of $R^{1'}$, $R^{2'}$ and $R^{3'}$ is a cyclic or heterocyclic acidic functional group having a pKa value below 8 or a group which is convertible in vivo to such a group;
$R^{4'}$, $R^{5'}$ and the two other substituents $R^{1'}$, $R^{2'}$ and $R^{3'}$ are each independently selected from hydrogen; alkyl; alkoxy; hydroxy; halogen; trifluoromethyl; cyano; nitro; amino; alkylamino; —$COOR^{7'}$; —$NHSO_2$-alkyl; —$SO_2N(R^{7'})_2$; —$SO_2OR^{7'}$; —CO—$R^{7'}$; aryl, biphenyl, phenylamino, phenoxy or heteroaryl, wherein the aryl, biphenyl, phenylamino, phenoxy or heteroaryl group may be substituted one or more times with substituents selected from alkyl, hydroxy, alkoxy, halogen, trifluoromethyl, cyano, nitro, amino and alkylamino; aryl and heteroaryl, or $R^{3'}$ and $R^{4'}$ or $R^{4'}$ and $R^{5'}$ together form a cyclic structure and the other substituents $R^{1'}$, $R^{2'}$, $R^{3'}$, $R^{4'}$ and $R^{5'}$ is as defined above;
and $R^{7'}$ is hydrogen, alkyl, amino or phenyl;
Y' is —CO—, —CS—, —$SO_2$—, or —C(=N—$R^{8'}$)—, wherein $R^{8'}$ is hydrogen, alkyl, or cyano;
X' is —NH—, —$CH_2$—NH—, or —$SO_2$—NH—;
Z is $NR^{6'}$, O, —CH=CH—, —N=CH—, or —CH=N—
$R^{6'}$ is hydrogen, or alkyl;
$R^{11'}$, $R^{12'}$, $R^{13'}$, $R^{14'}$ and $R^{15'}$ are each independently selected from hydrogen; alkyl; alkoxy; hydroxy; halogen; trifluoromethyl; cyano; nitro; amino; alkylamino; —$COOR^{7'}$; —$NHSO_2$-alkyl; —$SO_2N(R^{7'})_2$; —$SO_2OR^{7'}$; —CO—$R^{7'}$; aryl, biphenyl, phenylamino, phenoxy or heteroaryl, wherein the aryl, biphenyl, phenylamino, phenoxy or heteroaryl group may be substituted one or more times with substituents selected from alkyl, hydroxy, alkoxy, halogen, trifluoromethyl, cyano, nitro, amino and alkylamino; aryl and heteroaryl, or one of $R^{11'}$ and $R^{12'}$, $R^{12'}$ and $R^{13'}$, $R^{13'}$ and $R^{14'}$ and $R^{14'}$ and $R^{15'}$ together form a cyclic structure and the other substituents $R^{11'}$, $R^{12'}$, $R^{13'}$, $R^{13'}$ and $R^{15'}$ is as defined above and $R^{7'}$ is as defined above;
a compound as above wherein one of $R^{1'}$, $R^{2'}$ and $R^{3'}$ is 3-hydroxy-4-oxo-pyranyl, 2-hydroxy-4-oxo-pyrimidyl, 4-hydroxy-1,2,4-triazolyl, 3,5-dioxo-1,2,4-oxadiazolidinyl, 2,4-dioxo-imidazolidinyl, 2,5-dioxo-3-hydroxy-pyrrolyl, 2,5-dioxo-pyrrolidinyl, 2,4-dioxo-1,3-thiazolidinyl, 3-hydroxy-isoxazolyl, 5-hydroxy-isoxazolyl, 3-hydroxy-isothiazolyl, 3-hydroxy-1,2,5-thiadiazolyl, tetrazolyl, 3-hydroxy-triazolyl, 3-hydroxy-pyrazolyl, 2-hydroxy-1,3,4-oxadiazolyl or 2-hydroxy-3,4-dioxo-cyclobutenyl, 3-oxo-1,2-dihydro-1,2,4-trizaolyl, 2-oxo-3H-1,3,4-oxadizolyl, 3-oxo-1,2-dihydro-1,2,4-triazolyl; Z is $NR^{6'}$ and Y' is CO;
a compound as above, said compound being:
3-Trifluoromethylphenyl-4-nitro-2-(5-tetrazolyl)phenyl urea;
3-Trifluoromethylphenyl4-(2-naphthyl)-2-(5-tetrazolyl) phenyl urea;
3-Trifluoromethylphenyl-4-(3-pyridyl)-2-(5-tetrazolyl) phenyl urea;
3-Trifluoromethylphenyl-4-(1-naphthyl)-2-(5-tetrazolyl) phenyl urea;
3-Trifluoromethylphenyl-4-(4-trifluoromethylphenyl)-2-(5-tetrazolyl)phenyl urea;
3-Trifluoromethylphenyl-4-(3-furyl)-2-(5-tetrazolyl)phenyl urea;
3-Trifluoromethylphenyl-4-(3-thienyl)-2-(5-tetrazolyl) phenyl urea;
3-Trifluoromethylphenyl-4-(3-nitrophenyl)-2-(5-tetrazolyl) phenyl urea;
3-Trifluoromethylphenyl-4-(4-ethoxycarbonylphenyl)-2-(5-tetrazolyl)phenyl urea;
3-Trifluoromethylphenyl-4-(4-diethylaminocarbonylphenyl)-2-(5-tetrazolyl)phenyl urea;
3-Trifluoromethylphenyl-4-(4-aminocarbonylphenyl)-2-(5-tetrazolyl)phenyl urea;
3-Trifluoromethylphenyl-2-(4-hydroxy-1,2,4-triazol-3-yl) phenyl urea;
3-Trifluoromethylphenyl-2-(3-oxo-1,2-dihydro-1,2,4-triazol-1-yl)phenyl urea;
3-Trifluoromethylphenyl-2-(2-oxo-3H-1,3,4-oxadiazol-5-yl)phenyl urea;
3-Trifluoromethylphenyl-4-biphenylyl-2-(3-oxo-1,2-dihydro-1,2,4-triazol-1-yl)phenyl urea;
3-Trifluoromethylphenyl-4-amino-2-(5-tetrazolyl)phenyl urea;
3-Trifluoromethylphenyl-4-acetylamino-2-(5-tetrazolyl) phenyl urea;
3-Trifluoromethylphenyl-4-benzoylamino-2-(5-tetrazolyl) phenyl urea;
3-Trifluoromethylphenyl-4-(4-carboxyphenyl)-2-(5-tetrazolyl)phenyl urea;
3-Trifluoromethylphenyl-4-(4-anilinocarbonylphenyl)-2-(5-tetrazolyl)phenyl urea;
4-Biphenylyl-2-(5-tetrazolyl)phenyl urea;
3-Biphenylyl-2-(5-tetrazolyl)phenyl urea;
5-Indanyl-2-(5-tetrazolyl)phenyl urea;
3-Bromophenyl-4-bromo-2-(5-tetrazolyl)phenyl urea.
3-Acetylphenyl-2-(5-tetrazolyl)phenyl urea.
3-Biphenylyl-4-bromo-2-(5-tetrazolyl)phenyl urea.
3-(3-Pyridyl)phenyl-4-bromo-2-(5-tetrazolyl)phenyl urea.
Examples of pharmaceutically acceptable addition salts of the compounds of the invention include inorganic and organic acid addition salts such as the hydrochloride, hydrobromide, phosphate, nitrate, perchlorate, sulfate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2- sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Definition of Substituents

Halogen is fluorine, chlorine, bromine or iodine.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Alkoxy is O-alkyl, wherein alkyl is as defined above.

Amino is $NH_2$ or NH-alkyl or N-(alkyl)$_2$, wherein alkyl is as defined above. Acyl is —CO-alkyl wherein alkyl is as defined above.

Aryl is an aromatic hydrocarbon such as phenyl and naphtyl;

The acidic functional group having a pKa below 8 or a group which is converted in vivo to such group are groups such as 3-hydroxy-4-oxo-pyranyl, 2-hydroxy-4-oxo-pyrimidyl, 3,5-dioxo-1,2,4-oxadiazolidinyl, 2,4-dioxo-imidazolidinyl, 2,5-dioxo-3-hydroxy-pyrrolyl, 2,5-dioxo-pyrrolidinyl, 2,4-dioxo-1,3-thiazolidinyl, 3-hydroxy-isoxazolyi, 5-hydroxy-isoxazolyl, 3-hydroxy-isothiazolyl, 3-hydroxy-1,2,5-thiadiazolyl, tetrazolyl, 3-hydroxy-triazolyl, 3-hydroxy-pyrazolyl, 2-hydroxy-1,3,4-oxadiazolyl and 2-hydroxy-3,4-dioxo-cyclobutenyl, $NH_2$, —$COOR^{16}$, —$CH_2COOR^{16}$, —$CON(R^{16})_2$, —$NHSO_2$—$R^{16}$, —$SO_2N(R^{16})_2$, $SO_2OR^{16}$, —$PO_3H_2$, —$PO_3RH$, —$PO_2NH_2$, —CONHOH, —CONHCN, —$CONHSO_2R^{16}$ and —$CONHNH_2$, wherein $R^{16}$ is hydrogen, alkyl, cycloalkyl, cycloalkylalkyl, alkenyl, alkynyl, aryl or aralkyl, heteroaryl or $R^{16}$ comprises a 5-8 membered ring optionally containing double bonds and optionally containing one or two heteroatoms, or $R^{16}$ together with the heteroatom to which it is connected form a 5-8 membered ring optionally containing double bonds and optionally containing another heteroatom;

The cyclic or heterocyclic acidic group having a pKa below 8 or a group which is converted in vivo to such group are groups such as 3-hydroxy-4-oxo-pyranyl, 2-hydroxy-4-oxo-pyrimidyl, 3,5-dioxo-1,2,4-oxadiazolidinyl, 2,4-dioxo-imidazolidinyl, 2,5-dioxo-3-hydroxy-pyrrolyl, 2,5-dioxo-pyrrolidinyl, 2,4-dioxo-1,3-thiazolidinyl, 3-hydroxy-isoxazolyl, 5-hydroxy-isoxazolyl, 3-hydroxy-isothiazolyl, 3-hydroxy-1,2,5-thiadiazolyl, tetrazolyl, 3-hydroxy-triazolyl, 3-hydroxy-pyrazolyl, 2-hydroxy-1,3,4-oxadiazolyl, 4-hydroxy-1,2,4-triazolyl, 3-oxo-, 1,2-dihydro-1,2,4-triazolyl, 2-oxo-3H-1,3,4-oxadiazolyl, 3-oxo-1,2-dihydro-1,2,4-triazolyl and 2-hydroxy-3,4-dioxo-cyclobutenyl.

Heteroaryl is a 5- or 6-membered heterocyclic monocyclic group. Such a monocyclic heteroaryl group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 2-furyl, 3-furyl, 4-furyl, and 5-furyl.

A 5-8 membered ring optionally containing double bonds and optionally containing one or two heteroatoms includes for example pyrrolidine, piperidine, piperazine, morpholine, cyclohexyl, cyclohexen, dihydropyrrole, dihydrofuran, dihydrothiophen, dihydropyridine, dihydropyridazine, dihydropyrimidine, dihydropyrazine, tetrahydropyridine, tetrahydropyridazine, tetrahydropyrimidine, tetrahydropyrazine, homopiperazine, homopiperidine, azacyclooctane.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Steric Isomers

It will be appreciated by those skilled in the art that the compounds of the present invention contain several chiral centres and that such compounds exist in the form of isomers (i.e. enantiomers). The invention includes all such isomers and any mixtures thereof including racemic mixtures.

Some of the compounds of the present invention exist in (+) and (−) forms as well as in racemic forms. Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l-(tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Method of preparation

The compounds of the invention may be prepared in numerous ways. The compounds of the invention and their pharmaceutically acceptable derivatives may thus be prepared by any method as discribed above or known in the art for the preparation of compounds of analogous structure, and as shown in the representative examples which follow.

Biology

The compounds of the present invention are potent blockers of chloride channels in normal as well as sickle cell erythrocytes. The ability of the compounds to block the erythrocyte chloride channels can not be demonstrated by classical electrophysiological measurements such as patch clamping, since the channel unit conductance is below the detection limit of these techniques.

All dose-response experiments were therefore performed by concomitant measurements of conductive neffluxes of Cl$^-$ (J$_{Cl}$) and membrane potentials (V$_m$) in suspensions of erythrocytes (Bennekou, P. and Christophersen, P. (1986), Flux ratio of Valinomycin—Mediated K$^+$ Fluxes across the Human Red Cell Membrane in the presence of the Protronophore CCCP. J. Membrane Biol. 93, 221-227. ). The membrane Cl$^-$ conductances (G$_{Cl}$) were calculated by the following equation (Hodgkin, A. L. and Huxley, A. F. (1952) The components of membrane conductance in the giant axon of Loligo. J. Physiol. Lond. 116, 449-472):

$$G_{Cl} = \frac{F * J_{Cl}}{(V_m - E_{Cl})}$$

where F is the Faraday constant, E$_{Cl}$ is the Nernst potential for the Cl-ion. Administration of 3-Trifluoromethylphenyl-2-carboxyphenyl urea to a suspension of normal erythrocytes blocked G$_{Cl}$ more than 95% with a K$_D$-value of 1.3 $\mu$M. The compound equipotently blocked G$_{Cl}$ from oxygenated as well as deoxygenated homozygoteous sickle cell erythrocytes.

The K$_D$-value for for N-(3-Trifluoromethylphenyl)-N'-(4'-(N,N-dimethylsulfamoyl)-2-(1-H-tetrazol-5-yl)-4-biphenyl) urea in this test was 0.3 $\mu$M.

The K$_D$-value for for 3-Trifluoromethyl-4-bromo-2-(5-tetrazolyl)-phenylurea in this test was 1.9 $\mu$M.

Experimentally induced cell volume losses were measured as changes in the relative volume of packed cells. Inducing a massive water and salt loss (KCl) by addition the K$^+$-ionophore valinomycin to the suspension for 5 min reduced the cell volume by 26%. 3-Trifluoromethylphenyl-2-carboxyphenyl urea dose-dependently (IC$_{50}$-value of 1.2 $\mu$M) reduced the volume loss to 7%.

Deoxygenation induced permeability increases of sickle cells were estimated by measuring the extracellular K$^+$-concentration vs time. Normal erythrocytes exhibited very small K$^+$-fluxes, which was insensitive to deoxygenation and insensitive to 10 $\mu$M 3-Trifluoromethylphenyl-2-carboxyphenyl urea. The K$^+$ flux from oxygenated sickle erythrocytes was 2-3 times higher than from normal erythrocytes and these fluxes was accelerated 4-8 times upon deoxygenation. In presence of 3-Trifluoromethylphenyl-2-carboxyphenyl urea (10 $\mu$M) the basal K$^+$-flux from sickle erythrocytes was normalised and the deoxygenation induced flux component were nearly abolished.

3-Trifluoromethylphenyl-2-carboxyphenyl urea is non-toxic to mice and rats at concentrations up to 250 mg/kg i.p. and i.v.

The compounds of the present invention are useful as blockers of the bone degrading activity of osteoclasts. For measuring the activity of the compounds different osteoclast inhibition assays known in the art can be used.

Pharmaceutical Compositions

While it is possible that, for use in therapy, a compound of the invention may be administered as the raw chemical, it is preferable to present the active ingredient as a pharmaceutical formulation. Optionally the compounds of the invention can be administered together with another therapeutic compound. This can optionally be in the form of a pharmaceutical composition containing more than one compound.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization. When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Methods of Treating

The compounds of the present invention are very useful in the treatment of sickle cell anaemia, brain oedema following ischaemia or tumors, diarrhea, hypertension (diuretic), bone metabolic disorders, osteoclast associated disorders and glaucoma, due to their potent chloride channel blocking activity. These properties make the compounds of this invention extremely useful in the treatment of sickle cell anaemia, brain oedema following ischaemia or tumors, diarrhea, hypertension (diuretic), bone metabolic disorders, osteoclast associated disorders and glaucoma, as well as other disorders sensitive to the chloride channel blocking activity of the compounds of the present invention. The compounds of this invention may accordingly be administered to a living animal body, including a human, in need of treatment, alleviation, or elimination of an indication associated with or responsive to chloride channel blocking activity. This includes especially sickle cell anaemia, brain oedema following ischaemia, or tumors, diarrhea, hypertension (diuretic), bone metabolic disorders, osteoclast associated disorders and glaucoma.

Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge. When administered in combination with compounds known in the art for treatment of the diseases, the dosis regimen may be reduced.

The invention then comprises alone or in combination, the following:

the use of any of the compounds as mentioned above for the preparation of a medicament for the treatment of sickle-cell anaemia, brain oedema following ischaemia, or tumours, diarrhea, hypertension (diuretic), bone metabolism disorders, glaucoma, allergic or inflammatory conditions or healing ulcers;

the use of any of the compounds as above combined with the use of other bone metabolism controlling compounds for the treatment of bone metabolic disorders or conditions.

the use as above wherein the known compounds are bisphophonates such as etidronate, pamidronate, or clodronate optionally combined with calcium; oestrogen-receptor active compounds such as oestrogen i.e. oestradiol and ethyloestradiol, calcitonin, 1,25-dihydroxyvitamine D and metabolites thereof, fluoride, growth hormone, parathyreoidea hormone, triiodo-thyrosine, protease inhibitors ie. collagen degrading enzymes, or cancer therapeutic agents.

a method for the treatment of a disorder or disease of a living animal body which disorder or disease is sickle-cell anaemia, brain oedema following ischaemia or tumours, diarrhea, hypertension (diuretic), bone metabolic disorders, glaucoma, allergic or inflammatory conditions or ulcers, comprising administering to such a living animal body, including a human, in need thereof a therapeutically effective amount of a compound as any above;

a method for the treatment of a disorder or disease of a living animal body which disorder or disease is a bone metabolic disorder comprising administering to such a living animal body, including a human, in need thereof a therapeutically effective amount of a compound as any above optionally in combination with other bone metabolism controlling compounds.

In the context of this invention a bone metabolic disorder or disease covers any deviation in the bone formation and/or bone resorption as ie. osteoclast associated diseases or disorders, age related decrease in bone mass, osteoporosis, osteopeni, osteogenesis imperfecta, osteopetrosis, osteosklerosis, Paget's disease of bone, bone metastasizing cancers, osteomyelitis, osteonekrosis, fluorosis, bone malignancies etc. and covers in general all clinical types of the mentioned diseases;

In the context of this invention the compounds known for treatment for bone metabolic disorders includes bisphophonates such as etidronate, pamidronate, oestrogen-receptor binding compounds such as oestrogen i.e. oestradiol and ethyloestradiol; calcitonin, 1,25-dihydroxyvitamine D and metabolites thereof, fluoride, growth hormone, parathyroid hormone, triiodo-thyrosine, cancer therapeutic agents and inhibitors of collagen degrading enzymes such as protease inhibitors.

In the context of this invention the method of treatment of a disorder or disease of a living animal body including a human comprising administering a compound of the invention optionally together with a known compound and optionally administerering the compound(s) in a reduced dosis;

The treatment of the diseases and disorder can be in chronical or a long term treatment as well as a treatment of sudden crisis in the disease and disorder.

The following examples will illustrate the invention further, however, they are not to be construed as limiting.

EXAMPLE 1

N-3-Trifluoromethylphenyl-N'-2-carboxyphenyl Urea

3-Trifluoromethylphenyl isocyanate (1.87 g, 10 mmol) and 2-aminobenzoic acid (1.37 g, 10 mmol) were in toluene (50 mL) was stirred until the 2-aminobenzoic acid had been consumed. The product was filtered off. M.p. 171–172° C.

The following compounds were prepared analogously:

N-Phenyl-N'-(2-carboxyphenyl) urea. Mp. 168–169° C.

N-(3-Trifluoromethylphenyl)-N'-(2-carboxyphenyl)-N-methyl urea. Mp. 113–116° C.

N-(Trifluoromethylphenyl)-N'-(4-bromo-2-carboxyphenyl) urea. Mp. 177–178° C.

N-(Trifluoromethylphenyl)-N'-(2-carboxy-4-chlorophenyl) urea. Mp. 167–168° C.

N-(Trifluoromethylphenyl)-N'-(2-carboxy-4-fluorophenyl) urea. Mp. 176° C.

N-(3-Bromophenyl)-N'-(2-(1-H-tetrazol-5-yl)-4-biphenyl) urea. Mp. >240° C.

N-(3-Trifluoromethylphenyl)-N'-(4'-(N,N-dimethylsulfamoyl)-2-(1-H-tetrazol-5-yl)-4-biphenyl) urea. Mp. 258–260° C.

N-(3-Bromophenyl)-N'-(4'-(N,N-dimethylsulfamoyl)-2-(1-H-tetrazol-5-yl)-4-biphenyl) urea. Mp. 242–244° C.

N-(3-Bromophenyl)-N'-(4'-(N,N-dimethylcarbamoyl)-2-(1-H-tetrazol-5-yl)-4-biphenyl) urea. Mp. 173–175° C.

N-(3-Trifluoromethylphenyl)-N'-(4-amino-2-(1-H-tetrazol-5-yl)phenyl) urea. Mp. 175–180° C.

N-(3-Trifluoromethylphenyl)-N'-(4-acetylamino-2-(1-H-tetrazol-5-yl)phenyl) urea. Mp. 280–282° C.

N-(3-Trifluoromethylphenyl)-N'-(4'-carbamoyl-2-(1-H-tetrazol-5-yl)-4-biphenyl) urea. Mp. 252–253° C.

N-(3-Trifluoromethylphenyl)-N'-(4'-(N,N-dimethylcarbamoyl)-2-(1-H-tetrazol-5-yl)-4-biphenyl) urea. Mp.263–263° C.

N-(3-Trifluoromethylphenyl)-N'-(4'-carboxy-2-(1-H-tetrazol-5-yl)-4-biphenyl) urea. Mp. >300° C.

N-(3-Trifluoromethylphenyl)-N'-(4'-(N-phenylcarbamoyl)-2-(1H-tetrazol-5-yl)-4-biphenyl) urea. Mp. >300° C.

N-(2-Indan)-N'-(2-(1-H-tetrazol-5-yl)phenyl) urea. Mp. 154–157° C.

N-(4-Biphenyl)-N'-(2-(1-H-tetrazol-5-yl)phenyl) urea. Mp. 224–226° C.

N-(3-Biphenyl)-N'-(2-(1-H-tetrazol-5-yl)phenyl) urea. Mp. 189–191° C.

N-(3-Acetylphenyl)-N'-(2-(1-H-tetrazol-5-yl)phenyl) urea. Mp. 115–120° C.

N-(3-Trifluoromethylphenyl)-N'-(2-(1-methyltetrazol-5-yl)-4-biphenyl) urea. Mp. 170–171° C.

N-(3-Biphenyl)-N'-(4-bromo-2-(1-H-tetrazol-5-yl)phenyl) urea. Mp. 232–234° C.

N-(3-(3-Pyridyl)phenyl)-N'-(4-bromo-2-(1-H-tetrazol-5-yl) phenyl) urea hydrochloride. Mp.211–213° C.

N-(3-Bromophenyl)-N'-(4-bromo-2-(1-H-tetrazol-5-yl) phenyl) urea. Mp. >275° C.

N-(3-Bromophenyl)-N'-[3'-nitro-2-(1-H-tetrazol-5-yl) biphenyl] urea. Mp. 266–268° C.

N-(3-Bromophenyl)-N'-[4'-(sulfoamido-N-methylpiperazinium chloride)-2-(1-H-tetrazol-5-yl)-4-biphenyl] urea. Mp. 176–177° C.

N-(3-Bromophenyl)-N'-[4'-carbamoyl-N-methylpiperazine)-2-(1-H-tetrazol-5-yl)-4-biphenyl] urea. Mp. 155–158° C.

N-(3,5-Dichlorophenyl)-N'-[4-bromo-2-(1H-tetrazol-5-yl)phenyl] urea. Mp. 246–255° C.
N-(4-Trifluoromethylphenyl-N'-[4-bromo-2-(1-H-tetrazol-5-yl)phenyl] urea. Mp. 263–264° C.
N-(4-Bromophenyl)-N'-[4-bromo-2-(1-H-tetrazol-5-yl)phenyl] urea. Mp. 242–243° C.
N-(3-Methoxyphenyl)-N'-[4-bromo-2-(1-H-tetrazol-5-yl)phenyl] urea. Mp. 480–200° C.
N-(3-Chlorophenyl)-N'-[4-bromo-2-(1-H-tetrazol-5-yl)phenyl] urea. Mp. 254–256° C.
N-(3-Methylphenyl)-N'-[4-bromo-2-(1-H-tetrazol-5-yl)phenyl] urea. Mp. 258–263° C.
N-(3,4-Dichlorophenyl)-N'-[4-bromo-2-(1-H-tetrazol-5-yl)phenyl] urea. Mp. 228–231° C.
N-(2-Naphthyl)-N'-[4-bromo-2-(1-H-tetrazol-5-yl)phenyl] urea. Mp. 230° C. (decomp.)
N-(4-Methyl-3-nitrophenyl)-N'-[4-bromo-2-(1-H-tetrazol-5-yl)phenyl] urea. Mp. 231–234° C.
N-(2-Chloro-4-trifluoromethylphenyl)-N'-[4-bromo-2-(1-H-tetrazol-5-yl)phenyl] urea. Mp. 269–271° C.
N-(3,5-Di(trifluoromethyl)phenyl)-N'-[4-bromo-2-(1-H-tetrazol-5-yl)phenyl] urea. Mp. 268–271° C.
N-(3,5-Dichlorophenyl)-N'-[4-bromo-2-(1-H-tetrazol-5-yl)phenyl] urea. Mp. 258–268° C.
N-(4-Ethoxyophenyl)-N'-[4-bromo-2-(1-H-tetrazol-5-yl)phenyl] urea. Mp. 168–170° C.
N-(4-Methoxyphenyl)-N'-[4-bromo-2-(1H-tetrazol-5-yl)phenyl] urea. Mp. 215–218° C.
N-(2-Trifluoromethylphenyl)-N'-[4-bromo-2-(1-H-tetrazol-5-yl)phenyl] urea. Mp. 268–270° C.
N-(2-Bromophenyl)-N'-[4-bromo-2-(1-H-tetrazol-5-yl)phenyl] urea Mp. 277–279° C.
N-(2-Chlorophenyl)-N'-[4-bromo-2-(1-H-tetrazol-5-yl)phenyl] urea. Mp. 270–273° C.
N-(2-Fluorophenyl)-N'-[4-bromo-2-(1-H-tetrazol-5-yl)phenyl] urea. Mp. 270–273° C.
N-(4-Chloro-3-trifluoromethylphenyl)-N'-[4-bromo-2-(1H-tetrazol-5-yl)phenyl] urea Mp.259–261° C.
N-(3-Bromophenyl)-N'-(2,3-difluorophenyl) urea. Mp. 210–220° C.
N-(2-Methylphenyl)-N'-[4-bromo-2-(1-H-tetrazol-5-yl)phenyl] urea. Mp. 261–264° C.
N-(2-Ethylphenyl)-N'-[4-bromo-2-(1-H-tetrazol-5-yl)phenyl] urea. Mp. 272–273° C.
N-(4-Methylphenyl)-N'-[4-bromo-2-(1-H-tetrazol-5-yl)phenyl] urea. Mp. 253–254° C.
N-(2-Nitrophenyl)-N'-[4-bromo-2-(1-H-tetrazol-5-yl)phenyl] urea. Mp. 270–272° C.
N-(3-Fluorophenyl)-N'-[4-bromo-2-(1-H-tetrazol-yl)phenyl] urea. Mp. 269–271° C.
N-(4-[2-Propyl]phenyl)-N'-[4-bromo-2-(1-H-tetrazol-5yl)phenyl] urea. Mp. 233–237° C.
N-(3-Nitrophenyl)-N'-[4-bromo-2-(5-tetrazol-5-yl)phenyl] urea. Mp. 225–230° C.
N-(4-Nitrophenyl)-N'-[4-bromo-2-(1-H-tetrazol-5-yl)phenyl] urea. Mp. 233–235° C.

EXAMPLE 2

3-Trifluoromethylphenyl-4-bromo-2-(5-tetrazolyl)phenyl Urea

3-Trifluoromethylphenyl isocyanate (0.41 mL, 3.0 mmol) and 5-(2-amino-5-bromophenyl)tetrazole (0.6 g, 2.5 mmol) were added to toluene (10 mL). The reaction mixture was stirred at room temperature overnight. The precipitate was filtered and washed with toluene and then with petroleum ether to give 0.53 g of the desired compound. M.p. 269–270° C.

The following compounds were prepared analogously:
3-Trifluoromethylphenyl-2-(5-tetrazolyl)phenyl urea. M.p.257–258° C.
3-Trifluoromethylphenyl-2-(5-tetrazolyl)phenyl thiourea. M.p. >200° C. (dec.)
3-Trifluoromethylphenyl-4-phenyl-2-(5-tetrazolyl)phenyl urea. M.p. 260° C.
4-Trifluoromethylphenyl-2-(5-tetrazolyl)phenyl urea. M.p. 240° C. (dec.).
3-Chlorophenyl-2-(5-tetrazolyl)phenyl urea. M.p. 243° C. (dec.).
Phenyl-2-(5-tetrazolyl)phenyl urea. M.p. 239° C. (dec.).
3-Trifluoromethylphenyl-4-nitro-2-(5-tetrazolyl)phenyl urea. M.p. 204–205° C.
3-Trifluoromethylphenyl-4-(2-naphthyl)-2-(5-tetrazolyl)phenyl urea. M.p. 257–258° C.
3-Trifluoromethylphenyl-4-(3-pyridyl)-2-(5-tetrazolyl)phenyl urea. M.p. 148–152° C.
3-Trifluoromethylphenyl-4-(1-naphthyl)-2-(5-tetrazolyl)phenyl urea. M.p. 207–208° C.
3-Trifluoromethylphenyl-4-(4-trifluoromethylphenyl)-2-(5-tetrazolyl)phenyl urea. M.p. 135–140° C.
3-Trifluoromethylphenyl-4-(3-furyl)-2-(5-tetrazolyl)phenyl urea. M.p. 260–261° C.
3-Trifluoromethylphenyl-4-(3-thienyl)-2-(5-tetrazolyl)phenyl urea. M.p.259–260° C.
3-Trifluoromethylphenyl4-(3-nitrophenyl)-2-(5-tetrazolyl)phenyl urea. M.p. 135–140° C.
3-Trifluoromethylphenyl-4-(3-nitrophenyl)-2-(5-tetrazolyl)phenyl urea. M.p. 262–263° C.
3-Trifluoromethylphenyl-4-(4-diethylaminocarbonylphenyl)-2-(5-tetrazolyl)phenyl urea. M.p. 264–264° C.
3-Trifluoromethylphenyl-4-(4-aminocarbonylphenyl)-2-(5-tetrazolyl)phenyl urea. M.p. 252–253° C.
3-Trifluoromethylphenyl-2-(4-hydroxy-1,2,4-triazol-3-yl)phenyl urea. M.p. 220–221° C.
3-Trifluoromethylphenyl-2-(3-oxo-1,2-dihydro-1,2,4-triazol-1-yl)phenyl urea. M.p. >300° C.
3-Trifluoromethylphenyl-2-(2-oxo-3H-1,3,4-oxadiazol-5-yl)phenyl urea. M p. >300° C.
3-Trifluoromethylphenyl-4-biphenylyl-2-(3-oxo-1,2-dihydro-1,2,4-triazol-1-yl)phenyl urea. M.p.166° C.
3-Bromophenyl-4-bromo-2-(5-tetrazolyl)phenyl urea. M.p.142° C.

EXAMPLE 3

Intermediate

2-Chloro-5-hydroxybenzoic Acid

5-Amino-2-chlorobenzoic acid (85%, 10 g, 49.7 mmol) was suspended in diluted sulphuric acid (1.25%, 800 mL) and cooled to 5° C. on an ice bath. Sodium nitrite (5 g, 72 mmol) dissolved in water (150 mL) was added slowly while keeping the temperature of the reaction below 5° C. After addition of the sodium nitrite the reaction was stirred for another 45 min at 5–10° C. until a clear solution was obtained. The reaction mixture was poured into hot (70–85° C.) water (1.5 L), charcoal added and the reaction mixture heated at reflux for 25 min. Filtration and extraction with ethyl acetate afforded 6.7 g of the desired product as light brown crystals

EXAMPLE 4

Intermediate

2-Chloro-3-hydroxy-4-nitro-benzoic Acid

To a solution of 2-chloro-5-hydroxybenzoic acid (6.5 g, 38 mmol) in cold acetic acid (150 mL) was added concentrated nitric acid (2.7 mL, 38 mmol). After addition the reaction mixture was stirred for 30 min at room temperature then heated at 35° C. for 20 min. The reaction mixture was poured into ice and the product filtered off to give 1.5 g of the desired compound as yellow crystals.

EXAMPLE 5

Intermediate

4-Amino-6-chloro-3-hydroxybenzoic Acid

2-Chloro-3-hydroxy-4-nitro-benzoic acid (2.2 g, 10 mmol) dissolved in ethanol (120 mL) was reduced over Raney-Ni to give 1.7 g of black crystals.

EXAMPLE 6

Intermediate 5-(2-Aminophenyl)-1-H-tetrazole

2-Aminobenzonitrile (9.44 g, 80 mmol), sodium azide, (6.24 g, 0.1 mol), ammonium chloride (5.12 g, 0.1 mol) and dimethylformamide (50 mL) were mixed and heated at 120° C. overnight. The solvent was evaporated and the residue taken up in water. The crude product was isolated by filtration and re-crystallised from water. A yield of 8.4 g of pure product was obtained
Analogously were made:
5-(2-Amino-5-bromophenyl)-1-H-tetrazole
5-(4-Amino-3-biphenyl)-1-H-tetrazole
5-(2-Amino-5-nitrophenyl)-1-H-tetrazole
5-(2-Amino-5-(2-naphthyl)phenyl)-1-H-tetrazole
5-(2-Amino-5-(3-pyridyl)phenyl)-1-H-tetrazole
5-(2-Amino-5-(3-naphthyl)phenyl)-1-H-tetrazole
5-(2-Amino-5-(4-trifluoromethylphenyl)phenyl)-1-H-tetrazole
5-(2-Amino-5-(3-furyl)phenyl)-1-H-tetrazole
5-(2-Amino-5-(3-thienyl)phenyl)-1-H-tetrazole
5-(2-Amino-5-(4-trifluoromethylphenyl)phenyl)-1-H-tetrazole
5-(2-Amino-5-(3-nitrophenyl)phenyl)-1-H-tetrazole
5-(2-Amino-5-(4-ethoxycarbonylphenyl)phenyl)-1-H-tetrazole
5-(2-Amino-5-(4-diethylaminocarbonylphenyl)phenyl)-1-H-tetrazole
5-(2-Amino-5-(4-aminocarbonylphenyl)phenyl)-1-H-tetrazole
5-[2-Amino-5-(4-{sulfoamido-N'-methylpiperazine}phenyl)phenyl]-1-H-tetrazole
5-[2-Amino-5-(4-{carbamoyl-N'-methylpiperazine}phenyl)phenyl]-1-H-tetrazole
5-(2-Amino-4-(2-naphthyl)phenyl)tetrazole
5-(2-Amino-4-(3-pyridyl)phenyl)tetrazole
5-(2-Amino-4-(1-naphthyl)phenyl)tetrazole
5-(2-Amino-4-(4-trifluoromethylphenyl)phenyl)tetrazole
5-(2-Amino-4-(3-furyl)phenyl)tetrazole
5-(2-Amino-4-(3-thienyl)phenyl)tetrazole
5-(2-Amino-4-(4-trifluoromethylphenyl)phenyl)tetrazole
5-(2-Amino-4-(3-nitrophenyl)phenyl)tetrazole
5-(2-Amino-4-(4-ethoxycarbonylphenyl)phenyl)tetrazole
5-(2-Amino-4-(4-diethylaminocarbonylphenyl)phenyl)tetrazole
5-(2-Amino-4-(4-aminocarbonylphenyl)phenyl)tetrazole

EXAMPLE 7

Intermediate

2-Methylsulfonamidocarbonylaniline

Lithium methanesulfonamidate (1.0 g, 10 mmol) and isatoic anhydride (1.63 g, 10 mmol) in dimethyl sulfoxide (5 mL) were heated at 80° C. for 30 min. The reaction was cooled down to room temperature and acidified with hydrogen chloride in diethyl ether. The ether was evaporated and water added. The precipitated oil was purified by column chromatography on silica gel eluting with ethyl acetate/methanol (95:5). The desired material was obtained in a yield of 0.52 g.
Analogously were made;
2-phenylsulfonamidocarbonylaniline

EXAMPLE 8

Intermediate

Ethyl N-(2-bromoethyl)aminobenzoate

Dibromomethane (21.5 mL, 0.25 mol), ethyl-2-aminobenzoate (3.7 mL, 0.25 mmol) and triethylamine (4.2 mL, 30 mmol) were mixed in dimethylformamide (50 mL) and heated at 110° C. for five hours. After cooling to room temperature the reaction was poured onto ice and extracted with diethyl ether. The organic solution was washed with water, dried over magnesium sulphate and evaporated to dryness. The residue was purified by column chromatography on silica gel using dichloromethane as eluent to give 3.3 g of the desired material.

EXAMPLE 9

1-(3-Trifluoromethylphenyl)-3-(2-carboxyphenyl)-2-imidazolidone

To a solution of N-(3-trifluoromethylphenyl)-N'-(2-ethyloxycarbonylphenyl)-1,2-diaminoethane (1.1 g, 3.1 mmol) and triethylamine (1.1 mL, 7.5 mmol) in toluene was added phosgene in toluene (1.84 mL, 3.5 mmol). After stirring at room temperature for 30 min. Water and diethyl ether were added. The organic phase was dried and evaporated to dryness. The resulting residue was purified by column chromatography on silica gel using dichloromethane as eluent. The isolated ester (0.96 g) was hydrolysed in 4N aqueous sodium hydroxide to give the desired compound in a yield of 0.6 g. M.p. 197–198° C.

EXAMPLE 10

Intermediate

2-Amino-4-phenylbenzonitrile

A mixture of 2-amino-5-bromobenzonitrile (1.0 g, 5 mmol), phenylboronic acid (0.92 g, 7.5 mmol), tetrakis (triphenylphosphine)palladium (50 mg) and potassium carbonate (3.5 g, 25 mmol) in dimethoxyethane/water 2:1 (60 mL) was heated at reflux for 4 hours. After cooling to room temperature the reaction was diluted with water and extracted with ethyl acetate. The organic phase was dried and solvent evaporated. Trituation with petroleum ether gave 0.89 g of the desired compound.
Similarly was made;
2-Amino-5-(2-naphthyl)benzonitrile
2-Amino-5-(3-pyridyl)benzonitrile
2-Amino-5-(1-naphthyl)benzonitrile
2-Amino-5-(4-trifluoromethylphenyl)benzonitrile
2-Amino-5-(3-furyl)benzonitrile
2-Amino-5-(3-thienyl)benzonitrile
2-Amino-5-(3-nitrophenyl)benzonitrile
2-Amino-5-(4-ethoxycarbonylphenyl)benzonitrile
2-Amino-5-(4-diethylaminocarbonylphenyl)benzonitrile 2-Amino-5-(4-aminocarbonylphenyl)benzonitrile
1-(3-nitro-4-biphenylyl)-1,2-dihydro-1,2,4-triazol-3-one
2-Amino-5-(4-[sulfamido-N'-methylpiperazine]phenyl) benzonitrile 2-Amino-5-(4-[carbamoyl-N'-methylpiperazine]phenyl)benzonitrile
2-Amino-4-(2-naphthyl)benzonitrile
2-Amino-4-(3-pyridyl)benzonitrile
2-Amino-4-(1-naphthyl)benzonitrile
2-Amino-4-(4-trifluoromethylphenyl)benzonitrile
2-Amino-4-(3-furyl)benzonitrile
2-Amino-4-(3-thienyl)benzonitrile
2-Amino-4-(3-nitrophenyl)benzonitrile
2-Amino-4-(4-ethoxycarbonylphenyl)benzonitrile
2-Amino-4-(4-diethylaminocarbonylphenyl)benzonitrile
2-Amino-4-(4-am inocarbonylphenyl)benzonitrile

EXAMPLE 11

4-Methylphenylboronic Acid

To a solution of 4-iodotoluene (35 g, 160.5 mmol) in diethyl ether (400 mL) was added n-butyllithium (2 M in pentane, 88.3 mL, 176.6 mmol) at 0° C. After stirring at 0° C. for another 15 min the solution was cooled to –60° C. and tributylborate (60.6 mL, 224.7 mmol) was added. The cooling bath was removed and the reaction allowed to heat up to room temperature. The solution was acidified with hydrochloric acid (2 N, 280 mL) and the organic phase separated off. The aqueous phase was extracted with diethyl ether 2×125 mL). The combined organic phases were extracted with sodium hydroxide (1 N, 5×50 mL). The combined aqueous extracts were acidified to give 18.6 g of the desired material.

EXAMPLE 12

4-Carboxyphenylboronic Acid

To a solution of 4-methylphenylboronic acid (34 g, 0.25 mol) in aqueous sodium hydroxide (0.5 N, 1000 mL) was added potassium permanganate (83 g, 0.53 mol) while keeping the temperature at 35–40° C. After the addition the reaction was filtered and the filtrate acidified with concentrated hydrochloric acid (65 mL). The product was filtered off. A yield of 29.6 g was obtained. M.p. 228° C.

EXAMPLE 13

4-Ethoxycarbonylphenylboronic Acid

A solution of 4-carboxyphenylboronic acid (15 g, 0.09 mol), 99% ethanol (150 mL) and concentrated sulphuric acid (0.5 mL) was heated to reflux for two days. The volume was reduced to approximately 20 mL. The residue was triturated with petroleum ether to give 13.4 g of the desired material.

EXAMPLE 14

4-Aminocarbonylphenylboronic Acid

A solution of 4-carboxyphenylboronic acid (10 g, 0.06 mol) and thionyl chloride 875 mL) was heated to 50–60° C. overnight. The thionyl chloride was evaporated off. Half of the residue was added to concentrated ammonia (30 mL). The reaction was heated to reflux. Hot filtration and subsequent acidification of the filtrate yielded the crude material. The crude material was purified by suspending it in diluted sodium hydrogencarbonate to give 1.09 of the desired material.

Similarly was made;
4-Dimethylaminocarbonylphenylboronic Acid

EXAMPLE 15

4-Biphenylyl-2-(1-H-tetrazol-5-yl)phenyl Urea

To a solution of N,N-carbonyidiimidazole (0.96 g, 5.0 mmol) and imidazole (0.68 g, 10 mmol) in tetrahydrofuran (10 mL) at 0° C. was added 4-aminobiphenyl (1.0 g, 5.9 mmol) in tetrahydrofuran (10 mL). After stirring at 0° C. for 10 min 5-(2-aminophenyl)tetrazole (1.14 g, 7.1 mmol) was added. The reaction was stirred for another 4 hours and filtered. The filtrate was evaporated to dryness and the crude product purified by column chromatography. A yield of 0.28 g was obtained. M.p. 224–226° C.

Similarly was made;
3-biphenylyl-2-(1-H-tetrazol-5-yl)phenyl urea. M.p. 189–191° C.
5-indanyl-2-(1-H-tetrazol-5-yl)phenyl urea. M.p. 154–157° C.
3-Acetylphenyl-2-(5-tetrazolyl)phenyl urea. M.p. 115° C.
3-Biphenylyl-4-bromo-2-(5-tetrazolyl)phenyl urea.
3-(3-Pyridyl)phenyl-4-bromo-2-(5-tetrazolyl)phenyl urea.

EXAMPLE 16

3-Trifluoromethylphenyl-4-amino-2-(5-tetrazolyl)phenyl Urea

A solution of 3-trifluoromethylphenyl-4-nitro-2-(5-tetrazolyl)phenyl urea (0.8 g, 2.0 mmol) in 96% ethanol was hydrogenated over 5% palladium on charcoal for 3 hours at room temperature. The reaction mixture was filtered through a pad of celite and the solvent evaporated off to give 0.75 g of the desired product. M.p. 175–180° C.

EXAMPLE 17

3-Trifluoromethylphenyl-4-acetylamino-2-(5-tetrazolyl) phenyl Urea

To a solution of 3-trifluoromethylphenyl-4-amino-2-(5-tetrazolyl)phenyl urea (0.22 g, 0.6 mmol) in 17% aqueous sodium acetate (5 mL), cooled on an ice bath, was added acetic anhydride (1 mL). The reaction was stirred at 0° C. for another hour. The precipitate was filtered off and re-crystallised from 96% ethanol to give 0.12 g of the desired material. M.p. 280–282° C.

EXAMPLE 18

3-Trifluoromethylphenyl-4-benzoylamino-2-(5-tetrazolyl) phenyl Urea

To a solution of 3-trifluoromethylphenyl-4-amino-2-(5-tetrazolyl)phenyl urea (0.36 g, 1.0 mmol) in tetrahydrofuran (40 mL) was added triethylamine (0.17 mL, 1.2 mmol). The solution was cooled on an ice bath and benzoylchloride (0.14 mL, 1.2 mmol) was added. The reaction was stirred at 0° C. for another 30 min. The reaction was poured into water. The precipitate was filtered off and re-crystallised from 96% ethanol to give 0.28 g of the desired material. M.p. 271–272° C.

EXAMPLE 19

3-Trifluoromethylphenyl-4-(4-carboxyphenyl)-2-(5-tetrazolyl)phenyl Urea

To a suspension of 3-trifluoromethylphenyl-4-(4-ethoxycarbonylphenyl)-2-(5-tetrazolyl)phenyl urea (4.5 g, 9 mmol) in 96% ethanol was added sodium hydroxide (4 N, 25 mL). The reaction was heated to reflux for 30 min, then

EXAMPLE 20
3-Trifluoromethylphenyl-4-(4-anilinocarbonylphenyl)-2-(5-tetrazolyl)phenyl Urea A mixture of 3-trifluoromethylphenyl-4-(4-carboxyphenyl)-2-(5-tetrazolyl)phenyl urea (1.9 g, 4 mmol) and thionyl chloride (10 mL) was heated to 50° C. for 6 hours. The excess of thionyl chloride was evaporated off. Diethyl ether was added to the residue to give 2.2 g of solid material. Half of this material was suspended in tetrahydrofuran. Aniline (0.2 mL, 2.2 mmol) and triethylamine (0.5 mL, 3.6 mmol) were added. After stirring for 30 min the solvent was evaporated off. The residue was suspended in water and a small amount of diluted hydrochloric acid was added. The solid material was filtered off and re-crystallised from 96% ethanol to give 0.2 g of the desired material. M.p. >300° C.

EXAMPLE 21
4-Hydroxy-3-(2-aminophenyl)-[1,2,4]triazole

A solution of 4-hydroxy-3-(2-nitrophenyl)-1,2,4-triazole (0.38 g, 1.8 mmol), prepared according H.G.O. Becker in J. Prakt. Chem., 1970, 312, 610, in 96% ethanol was hydrogenated over 5% palladium on charcoal at room temperature for 1 hour. The reaction was filtered through a pad of celite to give desired material on evaporation of the solvent.

EXAMPLE 22
1-(4-Bromophenyl)-1,2-dihydro-[1,2,4]triazol-3-one

A mixture of 4-bromophenylhydrazine hydrochloride (5.0 g, 22.4 mmol) and urea (8.1 g, 134 mmol) was heated to 80° C. overnight in 1-methyl-2-pyrrolidinone (25 mL). The reaction was poured into water (250 mL) and concentrated ammonia was added until basic pH. The solution was cooled on an ice bath and the semicarbazone filtered off. The semicarbazone (1.0 g, 4,4 mmol) was stirred in triethyl orthoformiate (8 mL) at 90° C. for three days. The reaction mixture was cooled to room temperature and the crude material filtered off. Re-crystallisation from methanol afforded the desired product.

EXAMPLE 23
1-(4-Bromo-2-aminophenyl)-1,2-dihydro-1,2,4-triazol-3-one

To a solution of 1-(4-bromophenyl)-1,2-dihydro-[1,2,4]triazol-3-one (0.25 g, 1.0 mmol) in concentrated sulphuric acid (10 mL) at 0° C. was added potassium nitrate (0.13 g, 1.2 mmol). The reaction was stirred for another hour at 0° C. and the at room temperature overnight. The reaction mixture was poured into water and the precipitate filtered off to give 0.28 g of the desired nitro compound. The nitro compound (0.28 g, 1.0 mmol) suspended in 96% ethanol was hydrogenated over 5% palladium on charcoal to give the desired material.

EXAMPLE 24
5-(2-aminophenyl)-3H-1,3,4-oxadiazol-2-one

A solution of 2-nitrobenzoylhydrazine (9.05 g, 0.05 mol) in dioxane (30 mL) was slowly added to a solution of trichloromethyl chloroformate (4.6 mL, 0.04 mol) in dioxane (30 mL) at room temperature. On completion of the addition the reaction was heated to reflux for 4 hours. The solvent was evaporated off and the residue re-crystallised from 96% ethanol (50 mL) to give 7.15 g of the 5-(2-nitrophenyl)-3H-[1,3,4]oxadiazol-2-one. M.p. 157–158° C.

A solution of the nitro compound (2 g, 9.7 mmol) in 96% ethanol (25 mL) was hydrogenated over 5% palladium on charcoal to give desired 1.6 g of the desired amine.

EXAMPLE 25
1-(3-amino-4-biphenylyl)-1,2-dihydro-1,2,4-triazol-3-one

A solution of 1-(3-nitro-4-biphenylyl)-1,2-dihydro-1,2,4-triazol-3-one in 96% ethanol (25 mL) was hydrogenated over 5% palladium on charcoal to give the desired amine.

What is claimed is:
1. A compound having the formula

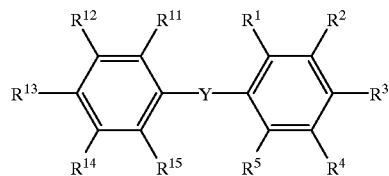

or a pharmaceutically acceptable salt thereof
wherein one of $R^1$, $R^2$ and $R^3$ is a heterocyclic acidic functional group having a pKa value below 8;
$R^4$, $R^5$ and the other two substituents $R^1$, $R^2$ and $R^3$ are each independently selected from hydrogen; alkyl; alkoxy; hydroxy; halogen; trifluoromethyl; cyano; nitro; amino; alkylamino, $NHCOR^9$, $CO_2R^9$, —CON$(R^9)_2$, —NHSO$_2$-$R^9$, —SO$_2$N$(R^9)_2$ wherein $R^9$ represents hydrogen, alkyl, cycloalkyl, cycloalkylalkyl, alkenyl, alkynyl, aryl, aralkyl, heteroaryl or $R^9$ comprises a 5–8 membered ring optionally containing double bonds and optionally containing one or two heteroatoms, which can be substituted by alkyl or acyl; or $(R^9)_2$ together with the heteroatom to which it is connected represents a 5–8 membered ring optionally containing double bonds and optionally containing another heteroatom which can be substituted by alkyl or acyl; aryl, phenylamino, phenoxy or heteroaryl wherein the phenyl, aryl or heteroaryl group may be substituted one or more times with substituents selected from alkyl, hydroxy, alkoxy, halogen, trifluoromethyl, cyano, nitro, amino, $NHCOR^9$, $CO_2R^9$, —CON$(R^9)_2$, —NHSO$_2$-$R^9$, —SO$_2$N$(R^9)_2$ wherein $R^9$ is as defined above; or $R^3$ and $R^4$ or $R^4$ and $R^5$ togethe form a 4–8 membered saturated or unsaturated ring and the other substituents $R^1$, $R^2$, $R^3$, $R^4$ and $R^5$ is as defined above;
Y represents

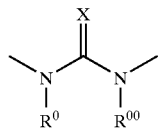

wherein $R^0$ and $R^{00}$ independently represents hydro en or lower alkyl;
X represents O or S;
$R^{11}$, $R^{12}$, $R^{13}$, $R^{14}$ and $R^2$ are each independently selected from hydrogen; alkyl; alkoxy; hydroxy; halogen; trifluoromethyl; cyano; nitro; amino; alkylamino; —COOR$^7$; —NHSO$_2$-alkyl; —SO$_2$N(R$^7$)$_2$; —SO$_2$OR$^7$; —CO—R$^7$; aryl, phenylamino, phenoxy or heteroaryl wherein the phenyl, aryl or heteroaryl group may be substituted one or more times with substituents selected from alkyl, hydroxy, alkoxy, halogen, trifluoromethyl, cyano, nitro, amino and alkylamino, —COOR$^7$; CON(R$^7$)$_2$—NHSO$_2$—R$^7$; —SO$_2$N(R$^7$)$_2$; —SO$_2$OR$^7$; —CO—R$^7$, or one of R¹¹ and R¹², R¹² and R¹³, R¹³ and R¹⁴ and R¹⁴ and R¹⁵ together form a 4–8 membered saturated or unsaturated ring and the other substituents R¹¹, R¹², R¹³, R¹⁴ and R¹⁵ is as defined above and wherein R⁷ represents hydrogen, alkyl, cycloalkyl, cycloalkylalkyl, alkenyl, alkynyl, aryl, aralkyl, heteroaryl or R⁷ comprises a 5–8 membered ring optionally containing double bonds and optionally containing one or two heteroatoms which can be substituted by alkyl or acyl; or (R⁷)₂ together with the heteroatom to which it is connected represents a 5–8 membered ring optionally containing double bonds and optionally containing another heteroatom which can be substituted by alkyl or acyl; with the proviso that the compound is not: N-[3-(2,5-dihydro-5-thioxo-1H-tetrazol-1yl)phenyl]—N'-[4-[5-[2-(hydroxmethyl)phenyl]-2-oxo-1,3,4-oxadiazol-3 (2H)-yl]phenyl urea; or N-[3 (2,5-dihydro-5-thioxo-1H-tetrazol-1yl)phenyl-N'-[4-(2-oxo-1,3,4-oxadiazol-3(2H)-yl)phenyl]-urea.

2. A compound according to claim 1 wherein one of R¹, R² and R³ is 3-hydroxy-4-oxo-pyranyl, 2-hydroxy-4-oxo-pyrimidyl 3, 5-dioxo-1,2,4-oxadiazolidinyl, 2,4-dioxo-imidazolidinyl, 2,5-dioxo-3-hydioxy-pyrrolyl, 2,5-dioxo-pyrrolidinyl, 2,4-dioxo-1,3--thiazolidinyl, 3-hydroxy-isoxazolyl, 5-hydroxy-isoxazolyl, 3-hydroxy-isothiazolyl, 3-hydroxy-1,2, 5-thiadiazolyl, tetrazolyl, 3-hydroxy-triazolyl, 3-hydroxy-pyrazolyl, or 2-hydroxy-1, 3,4-oxadiazolyl, and the other of R¹, R² and R³ is as defined in claim 1.

3. A compound according to claim 1 wherein one of R¹, R² and R³ represents tetrazolyl or methyltetrazolyl.

4. A compound according to claim 1 wherein R⁴, R⁵ and the remaining of R¹, R² or R³ independently represents hydrogen, alkyl, nitro, amino, alkylamino, CO₂R⁹, CF₃, alkyl, halogen, hydroxy, alkoxy, NHCOR⁹, —CON(R⁹)₂, aryl optionally substituted with NO₂, CON(R⁹)₂, NHCOR⁶, SO₂N(R⁹)₂, CO₂R⁹, wherein R⁹ is as defined in claim 1.

5. A compound according to claim 1 wherein one or more of R¹¹, R², R¹³, R¹⁴ and R¹⁵ independently represents CF₃, halogen, alkyl, alkoxy, NO₂, COON, SO₂OR⁷ or aryl optionally substituted with CO₂R⁷, —CON(R⁷)₂, —NHSO₂—R⁷, —SO₂N(R⁷)₂ wherein R⁷ is as defined in claim 1; or R¹¹ and R¹² together with the phenyl group to which they are attached forms a 6-membered unsaturated ring.

6. A compound according to claim 1, said compound being
N-(3-bromophenyl)—N'-(2- (l-H-tetrazol-5-yl)-4-biphenyl) urea;
N-(3-trifluoromethylphenyl)+N'-(4'-(N,N-dimethylsulfamoyl) -2-(1-H-tetrazol-5-yl)-4-biphenyl) urea;
N-(3-bromophenyl)—N'-(4'-(N,N-dimethylsulfamoyl) -2-1-H-tetrazol-5-yl) -4-biphenyl) urea;
N-(3-bromophenyl) —N'-(4'-(N,N-dimethylcarbamoyl) -2-1-H-tetrazol-5-yl) -4-biphenyl) urea;
N-(3-trifluoromethylphenyl) -N'- (4'-(N,N-dimethylcarbamoyl)-2-(1-H-tetrazol-5-yl)-4-biphenyl) urea;
N-(2-indan)-N'-(2-(l-H-tetrazol-5-yl)phenyl) urea;
N-(3-trifluoromethylphenyl)—N'-(2-(1-methyltetrazo-5-yl)-4-biphenyl) urea;
N-3-trifluoromethylphenyl-N'-(4-(4-benzoylcarbonyl henyl)- 2-(1-H-tetrazol-5-yl) phenyl urea;
N-(3-Bromophenyl)—N'-[3-nitro-2-(1-H-tetrazol-5-yl) biphenyl]urea;
N-(3-Bromophenyl)—N'-[4'-(sulfoamido-N-methylpiperazinium chloride)-2-(1-H-tetrazol-5-yl)-4-biphenyl]urea;
N-(3-Bromophenyl)—N'- [4'-carbamoyl-N-methylpiperazine) -2- (1-H-tetrazol-5-yl) -4-biphenyl] urea;
N-(4-Trifluoromethylphenyl-N'-[4-bromo-2- (1-H-tetra ol-5-yl)phenyl]]urea;
N-(4-Bromophenyl)—N'- [4-bromo-2- (1-H-tetrazol-5-yl) phenyl]urea;
N-(3-Methoxyphenyl)—N'- [4-bromo-2- (1-H-tetrazol-5-1) phenyl]urea;
N-(3-Chiorophenyl)—N'- [4-bromo-2- (1-H-tetrazol-5-ylphenyl]urea;
N-(3-Methyiphenyl)—N'-[4-bromo-2- (1-H-tetrazol-5-yl) phenyl] urea;
N-(2-Naphthyl)—N'- [4-bromo-2- (1-H-tetrazol-5-yl) phenyl] urea;
N-(4-Ethoxyophenyl)—N'- [4-bromo-2- (1-H-tetrazol-5-1) phenyl] urea;
N-(4-Methoxyphenyl)—N'- [4-bromo-2- (1H-tetrazol-5-yl) phenyl] urea;
N-(2-Trifluoromethylphenyl)—N'- [ 4-bromo-2- (1-H-tetrazol-5-yl)phenyl] urea;
N-(2-Bromophenyl)—N'- [4-bromo-2- (1-H-tetrazol-5-yl) phenyl] urea;
N-(2-Chlorophenyl)—N'- [4-bromo-2- (1-H-tetrazol-5-yl) phenyl] urea;
N-(2-Fluorophenyl)—N'- [4-bromo-2- (1-H-tetrazol-5-yl) phenyl] urea;
N-(2-Methylphenyl)—N'- [4-bromo-2- (1-H-tetrazol-5-yl) phenyl] urea;
N-(2-Ethylphenyl)—N'- [ 4-bromo-2- (1-H-tetrazol-5-yl) phenyl] urea;
N-(4-Methylphenyl)—N'- [4-bromo-2- (1-H-tetrazol-5-yl) phenyl] urea;
N-(2-Nitrophenyl)—N'- [4-bromo-2- (1-H-tetrazol-5-yl) phenyl] urea;
N-(3-Fluorophenyl)—N'- [4-bromo-2- (1-H-tetrazol-yl) phenyl] urea;
N-(4- [2-Propyl]phenyl)—N'- [4-bromo-2- (1-H-tetrazol 5yl)phenyl] urea;
N-(3-Nitrophenyl)—N'- [4-bromo-2- (5-tetrazol-5-yl) phenyl] urea;
N-(3-Acetyiphenyl)—N'- [4-bromo-2- (1-H-tetrazol-5-yl) phenyl] urea; or
N-(4-Nitrophenyl)—N'- [4-bromo-2- (1-H-tetrazol-5-yl) phenyl] urea; and pharmaceutically acceptable addition salts of any of the compounds above.

7. A method for the preparation of a compound of claim 1, comprising:

a) reacting a compound having the formula

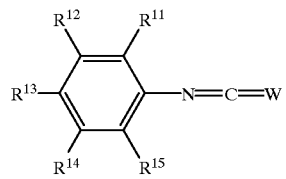

wherein W is O, or S and R¹¹, R¹², R¹³, R¹⁴ and R¹⁵ is as defined above, with a compound having the formula

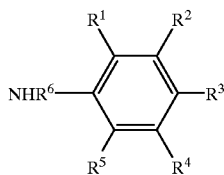

wherein $R^1$, $R^2$, $R^3$, $R^4$, $R^5$ is as defined above and $R^6$ is hydrogen, or alkyl, or b) reacting a compound having the formula

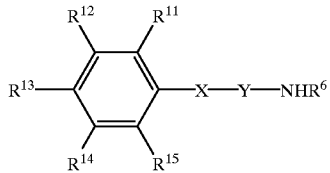

wherein X, Y, $R^6$, $R^{11}$, $R^{12}$, $R^{13}$, $R^{14}$ and $R^{15}$ is as defined above, with a compound having the formula

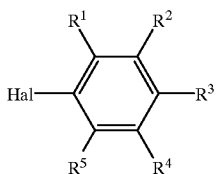

wherein Hal is halogen and $R^1$, $R^2$, $R^3$, $R^4$ and $R^5$ is a defined above, whereafter optionally the compound obtained is converted to another compound of the invention and/or a pharmaceutically acceptable salt thereof is formed using conventional methods.

8. A pharmaceutical composition comprising a chloride channel blocker according to claim 1, combined with one or more compounds known for treatment for bone metabolic disorders or pharmaceutically acceptable salt of these compounds, together with at least one pharmaceutically acceptable carrier or diluent.

9. A pharmaceutical composition comprising a therapeutically effective amount of a compound according to claim 1 or a pharmaceutically acceptable salt thereof together with at least one pharmaceutically acceptable carrier or diluent.

10. A method for the treatment of a disorder or disease of a living animal body, including a human, which disorder or disease is responsive to the blockade of chloride channels, comprising administering to such a living animal body in need thereof a therapeutically effective amount of a compound according to claim 1.

11. A method for the treatment of a disorder or disease of a living animal body which disorder or disease is sickle-cell anaemia, brain oedema following ischaemia or tumours, diarrhea, hypertension, bone metabolic disorders, osteoclast associated disorders, bone metastasizing cancer, glaucoma, allergic or inflammatory conditions or ulcers, comprising administering to such a living animal body, including a human, in need thereof a therapeutically effective amount of a compound of claim 1.

12. A method for the treatment of a disorder or disease of a living animal body which disorder or disease is a bone metabolic disorder comprising administering to such a living animal body, including a human, in need thereof a therapeutically effective amount of a or more compounds according to claim 1, optionally in combination with a therapeutically effective amount of one or more compounds known for treatment for bone metabolic disorders.

13. A compound having the formula

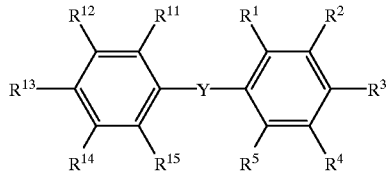

or a pharmaceutically acceptable salt thereof
wherein one of $R^1$, $R^2$ and $R^3$ is 3-hydroxy-4-oxo-pyranyl, 2-hydroxy-4-oxo-pyrimidyl, 3,5-dioxo-1,2,4-oxadiazolidinyl, 2,4-dioxo-imidazolidinyl, 2,5-dioxo-3-hydroxy-pyrrolyl 2,5-dioxo-pyrrolidinyl, 2,4-dioxo-1,3-thiazolidinyl, 3-hydroxy-isoxazolyl, 5-hydroxy-isoxazolyl, 3-hydroxy-isothiazolyl, 3 hydroxy-1,2, 5thiadiazolyl, tetrazolyl, 3-hydroxy-triazolyl, 3-hydroxy-pyrazolyl, or 2-hydroxy-1,3,4-oxadiazolyl; $R^4$, $R^5$ and the other two substituents $R^1$, $R^2$ and $R^3$ are each independently selected from hydrogen; alkyl; alkoxy; hydroxy; halogen; trifluoromethyl; cyano; nitro; amino; alkylamino, $NHCOR^9$, $CO_2R^9$, —CON $(R^9)_2$, —$NHSO_2$-$R^9$, —$SO_2N(R^9)_2$ wherein $R^9$ represents hydrogen, alkyl, cycloalkyl, cycloalkylalkyl, alkenyl, alkyny, aryl, aralkyl, heteroaryl or $R^9$ comprises a 5–8 membered ring optionally containing double bonds and optionally containing one or two heteroatoms, which can be substituted by alkyl or acyl; or $(R^9)_2$ together with the heteroatom to which it is connected represents a 5–8 membered ring optionally containing double bonds and optionally containing another heteroatom which can be substituted by alkyl or acyl; aryl, phenylamino, phenoxy or heteroaryl wherein the phenyl, aryl or heteroaryl group may be substituted one or more times with substituents selected from alkyl, hydroxy, alkoxy, halogen, trifluoromethyl, cyano, nitro, amino, $NHCOR^9$, $CO_2R^9$, —$CON(R^9)_2$, —$NHSO_2$-$R^9$, —$SO_2N(R^9)_2$ wherein $R^9$ is as defined above; or $R^3$ and $R^4$ or $R^4$ and $R^5$ together form a 4–8 membered saturated or unsaturated ring and the other substituents $R^1$, $R^2$, $R^3$, $R^4$ and $R^5$ is as defined above;
Y represents

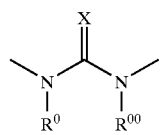

wherein $R^0$ and $R^{00}$ independently represents hydrogen or lower alkyl;
X represents O or S;
$R^{11}$, $R^{12}$, $R^{13}$, $R^{14}$ and $R^{15}$ are each independently selected from hydrogen; alkyl; alkoxy; hydroxy; halogen; trifluoromethyl; cyano; nitro; amino; alkylamino; —$COOR^7$; —$NHSO_2$-alkyl; —$SO_2N(R^7)_2$; —$SO_2OR^7$; —CO—$R^7$; aryl, phenylamino, phenoxy or heteroaryl wherein the phenyl, aryl or heteroaryl group may be substituted one or more times with substituents selected from alkyl, hydroxy, alkoxy, halogen, trifluoromethyl, cyano, nitro, amino and alkylamino, —COOR $^7$; $CON(R^7)_2$, —$NHSO_2$—$R^7$; —$SO_2N(R^7)_2$; —$SO_2OR^7$; —CO—$R^7$, or one of $R^{11}$ and $R^{12}$, $R^{12}$ and $R^{13}$, $R^{13}$ and $R^{14}$ and $R^{14}$ and $R^{15}$ together form a 4–8 membered saturated or unsaturated ring and the other substituents $R^{11}$, $R^{12}$, $R^{13}$, $R^{14}$ and $R^{15}$ is as defined above and wherein $R^7$ represents hydrogen, alkyl, cycloalkyl, cycloalkylalkyl, alkenyl, alkynyl, aryl, aralkyl, heteroaryl or $R^7$ comprises a 5–8 membered ring optionally containing double bonds and optionally containing one or two heteroatom which can be substituted by alkyl or acyl; or $(R^7)_2$ together with the heteroatom to which it is connected represents a 5–8 membered ring optionally containing double bonds and optionally containing another heteroatom which can be substituted by alkyl or acyl.

* * * * *